(12) United States Patent
Moyo et al.

(10) Patent No.: US 9,518,130 B2
(45) Date of Patent: *Dec. 13, 2016

(54) USE OF ERBB3 INHIBITORS IN THE TREATMENT OF TRIPLE NEGATIVE AND BASAL-LIKE BREAST CANCERS

(71) Applicant: Merrimack Pharmaceuticals, Inc., Cambridge, MA (US)

(72) Inventors: Victor Moyo, Ringoes, NJ (US); Gabriela Garcia, Roslindale, MA (US)

(73) Assignee: Merrimack Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/518,900

(22) Filed: Oct. 20, 2014

(65) Prior Publication Data

US 2015/0132292 A1  May 14, 2015

Related U.S. Application Data

(63) Continuation of application No. 13/583,949, filed as application No. PCT/US2011/028159 on Mar. 11, 2011, now Pat. No. 8,895,001.

(60) Provisional application No. 61/312,895, filed on Mar. 11, 2010.

(51) Int. Cl.
| | |
|---|---|
| *A61K 39/395* | (2006.01) |
| *C07K 16/30* | (2006.01) |
| *C07K 16/40* | (2006.01) |
| *A61K 31/337* | (2006.01) |
| *A61K 31/517* | (2006.01) |
| *A61K 45/06* | (2006.01) |
| *C07K 16/28* | (2006.01) |
| *C07K 16/32* | (2006.01) |
| *C07K 16/22* | (2006.01) |
| *A61K 39/00* | (2006.01) |

(52) U.S. Cl.
CPC .......... *C07K 16/40* (2013.01); *A61K 31/337* (2013.01); *A61K 31/517* (2013.01); *A61K 39/3955* (2013.01); *A61K 39/39558* (2013.01); *A61K 45/06* (2013.01); *C07K 16/22* (2013.01); *C07K 16/2863* (2013.01); *C07K 16/3015* (2013.01); *C07K 16/32* (2013.01); *A61K 2039/505* (2013.01); *A61K 2039/507* (2013.01); *C07K 2317/21* (2013.01); *C07K 2317/73* (2013.01); *C07K 2317/76* (2013.01)

(58) Field of Classification Search
CPC ................. A61K 39/395; A61K 39/39558
See application file for complete search history.

(56) References Cited

U.S. PATENT DOCUMENTS

| | | | |
|---|---|---|---|
| 5,344,760 | A | 9/1994 | Harvey et al. |
| 5,480,968 | A | 1/1996 | Kraus et al. |
| 5,968,511 | A | 10/1999 | Akita et al. |
| 6,696,290 | B2 | 2/2004 | Fitzpatrick et al. |
| 6,983,227 | B1 | 1/2006 | Thalhammer-Reyero |
| 7,097,840 | B2 | 8/2006 | Erickson et al. |
| 7,125,680 | B2 | 10/2006 | Singer et al. |
| 7,285,649 | B2 | 10/2007 | Akita et al. |
| 7,314,916 | B2 | 1/2008 | Singer et al. |
| 7,390,632 | B2 | 6/2008 | Maihle et al. |
| 7,589,180 | B2 | 9/2009 | Old et al. |
| 7,638,303 | B2 | 12/2009 | Maihle et al. |
| 7,846,440 | B2 | 12/2010 | Schoeberl et al. |
| 8,268,793 | B2 | 9/2012 | Hedtjarn |
| 8,476,409 | B2 | 7/2013 | Baum et al. |
| 8,623,592 | B2 | 1/2014 | Schoeberl et al. |
| 8,691,225 | B2 | 4/2014 | Schoeberl et al. |
| 8,877,687 | B2 | 11/2014 | Song et al. |
| 8,895,001 | B2 | 11/2014 | Moyo et al. |
| 8,927,694 | B2 | 1/2015 | McDonagh et al. |
| 8,961,966 | B2 | 2/2015 | Schoeberl et al. |
| 9,011,851 | B2 | 4/2015 | Ullrich et al. |

(Continued)

FOREIGN PATENT DOCUMENTS

| | | |
|---|---|---|
| EP | 0896586 B1 | 2/1999 |
| EP | 1058562 B1 | 12/2000 |
| EP | 1187634 B1 | 3/2002 |
| EP | 1283053 A1 | 2/2003 |
| EP | 1351744 B1 | 10/2003 |
| EP | 1414494 B1 | 5/2004 |
| EP | 1728802 A2 | 12/2006 |
| EP | 1889631 A1 | 2/2008 |
| EP | 2067792 A2 | 6/2009 |
| JP | 2009500005 A | 1/2009 |

(Continued)

OTHER PUBLICATIONS

Petrelli et al., Expert Opin. Investig. Drugs, 2009; 18:1467-77.*

(Continued)

*Primary Examiner* — Jessica H Roark
(74) *Attorney, Agent, or Firm* — Nelson Mullins Riley & Scarborough LLP; Jane E. Remillard, Esq.; Jill Gorny Sloper, Esq.

(57) ABSTRACT

Provided are methods of suppressing growth of triple negative breast tumors and basal-like breast tumors by contacting tumor cells with an ErbB3 inhibitor, e.g., an anti-ErbB3 antibody. Also provided are methods for treating triple negative breast cancer or basal-like breast cancer in a patient by administering to the patient an ErbB3 inhibitor, e.g., an anti-ErbB3 antibody. The treatment methods can further comprise selecting a patient having a triple negative breast cancer or basal-like breast cancer and then administering an ErbB3 inhibitor to the patient. The treatment methods also can further comprise administering at least one additional anti-cancer agent to the patient in combination with the ErbB3 inhibitor.

22 Claims, 5 Drawing Sheets

(56) References Cited

U.S. PATENT DOCUMENTS

| | | |
|---|---|---|
| 2002/0001587 A1 | 1/2002 | Erickson et al. |
| 2002/0002276 A1 | 1/2002 | Fitzpatrick et al. |
| 2002/0009740 A1 | 1/2002 | Kaddurah-Daouk et al. |
| 2002/0119148 A1 | 8/2002 | Gerritsen et al. |
| 2002/0165193 A1 | 11/2002 | Greene et al. |
| 2003/0040605 A1 | 2/2003 | Siegel |
| 2003/0199020 A1 | 10/2003 | Fitzpatrick et al. |
| 2004/0052786 A1 | 3/2004 | Gerritsen et al. |
| 2004/0071696 A1 | 4/2004 | Adams et al. |
| 2004/0082510 A1 | 4/2004 | Ullrich et al. |
| 2004/0138417 A1 | 7/2004 | Fitzpatrick et al. |
| 2004/0197332 A1 | 10/2004 | Ullrich et al. |
| 2004/0229380 A1 | 11/2004 | Chan-Hui et al. |
| 2004/0248151 A1 | 12/2004 | Bacus et al. |
| 2004/0248196 A1 | 12/2004 | Adams et al. |
| 2005/0004018 A1 | 1/2005 | Jimeno et al. |
| 2005/0079184 A1 | 4/2005 | Hsing-Chang et al. |
| 2005/0187745 A1 | 8/2005 | Lurie et al. |
| 2005/0267720 A1 | 12/2005 | Hill et al. |
| 2006/0040363 A1 | 2/2006 | Kucherlapati et al. |
| 2006/0093603 A1 | 5/2006 | Gerritsen et al. |
| 2006/0127928 A1 | 6/2006 | Bacus et al. |
| 2006/0136139 A1 | 6/2006 | Elcock et al. |
| 2006/0167637 A1 | 7/2006 | Agur et al. |
| 2006/0177907 A1 | 8/2006 | Singer et al. |
| 2006/0204505 A1 | 9/2006 | Sliwkowski et al. |
| 2006/0210561 A1 | 9/2006 | Baughman et al. |
| 2007/0059785 A1 | 3/2007 | Bacus et al. |
| 2007/0081994 A1 | 4/2007 | Fitzpatrick et al. |
| 2007/0092513 A1 | 4/2007 | Gerritsen et al. |
| 2007/0122407 A1 | 5/2007 | Akita et al. |
| 2007/0134251 A1 | 6/2007 | Ashkenazi et al. |
| 2007/0134252 A1 | 6/2007 | Bacus et al. |
| 2007/0190583 A1 | 8/2007 | Spector et al. |
| 2007/0254295 A1 | 11/2007 | Harvey et al. |
| 2008/0026415 A1 | 1/2008 | Rimm et al. |
| 2008/0057064 A1 | 3/2008 | Zhou |
| 2008/0090233 A1 | 4/2008 | Garcia et al. |
| 2008/0112958 A1 | 5/2008 | Mass |
| 2008/0124334 A1 | 5/2008 | Akita et al. |
| 2008/0124345 A1 | 5/2008 | Rothe et al. |
| 2008/0187948 A1 | 8/2008 | Chan-Hui et al. |
| 2008/0207615 A1 | 8/2008 | Bell et al. |
| 2008/0214584 A1 | 9/2008 | Ohta et al. |
| 2008/0254497 A1 | 10/2008 | Singh |
| 2008/0261270 A1 | 10/2008 | Maihle et al. |
| 2008/0274504 A1 | 11/2008 | Maihle et al. |
| 2008/0318894 A1 | 12/2008 | Hedtjarn |
| 2009/0061422 A1 | 3/2009 | Linke et al. |
| 2009/0181022 A1 | 7/2009 | Nielsen et al. |
| 2009/0246206 A1 | 10/2009 | Nielsen et al. |
| 2009/0291085 A1 | 11/2009 | Schoeberl et al. |
| 2010/0056761 A1 | 3/2010 | Schoeberl et al. |
| 2010/0158894 A1 | 6/2010 | Umemura et al. |
| 2010/0178651 A1 | 7/2010 | Hatzis et al. |
| 2011/0027291 A1 | 2/2011 | Schoeberl et al. |
| 2011/0123523 A1 | 5/2011 | Schoeberl et al. |
| 2011/0159513 A1 | 6/2011 | Schoeberl et al. |
| 2012/0225870 A1 | 9/2012 | Janne et al. |
| 2012/0244163 A1 | 9/2012 | Schoeberl et al. |
| 2013/0034745 A1 | 2/2013 | Moyo et al. |
| 2013/0236459 A1 | 9/2013 | Baum et al. |
| 2014/0017264 A1 | 1/2014 | McDonagh et al. |
| 2014/0056898 A1 | 2/2014 | Zhang et al. |
| 2014/0079703 A1 | 3/2014 | Zhang et al. |
| 2014/0127238 A1 | 5/2014 | Schoeberl et al. |
| 2014/0134170 A1 | 5/2014 | Garcia et al. |
| 2014/0234317 A1 | 8/2014 | Onsum et al. |
| 2014/0234329 A1 | 8/2014 | Schoeberl et al. |
| 2014/0248280 A1 | 9/2014 | Kubasek et al. |
| 2014/0271665 A1 | 9/2014 | Aftab et al. |
| 2015/0132292 A1 | 5/2015 | Moyo et al. |
| 2015/0231238 A1 | 8/2015 | Garcia et al. |
| 2016/0090418 A1 | 3/2016 | Adiwijaya et al. |

FOREIGN PATENT DOCUMENTS

| | | |
|---|---|---|
| WO | 97/35885 A1 | 10/1997 |
| WO | 98/02540 A1 | 1/1998 |
| WO | 99/54800 A2 | 10/1999 |
| WO | 99/60023 A1 | 11/1999 |
| WO | 00/78347 A1 | 12/2000 |
| WO | 02/18444 A2 | 3/2002 |
| WO | 02/060470 A1 | 8/2002 |
| WO | 02060470 A1 | 8/2002 |
| WO | 03/012072 A2 | 2/2003 |
| WO | 03/013602 A1 | 2/2003 |
| WO | 03012072 A2 | 2/2003 |
| WO | 03013602 A1 | 2/2003 |
| WO | 2004/003019 A3 | 1/2004 |
| WO | 2004/053497 A2 | 6/2004 |
| WO | 2004/091384 A2 | 10/2004 |
| WO | 2005/017493 A2 | 2/2005 |
| WO | 2006/017538 A2 | 2/2006 |
| WO | 2006/020706 A2 | 2/2006 |
| WO | 2006/044748 A2 | 4/2006 |
| WO | 2006/063042 A2 | 6/2006 |
| WO | 2006/091209 A2 | 8/2006 |
| WO | 2007/015935 A2 | 2/2007 |
| WO | 2007/039705 A1 | 4/2007 |
| WO | 2007/041502 A2 | 4/2007 |
| WO | 2007/077028 A2 | 7/2007 |
| WO | 2007/115571 A2 | 10/2007 |
| WO | 2007/130677 A2 | 11/2007 |
| WO | 2008/032876 A1 | 3/2008 |
| WO | 2008/064884 A1 | 6/2008 |
| WO | 2008/100624 A2 | 8/2008 |
| WO | 2008/109440 A2 | 9/2008 |
| WO | 2009/126920 A2 | 10/2009 |
| WO | 2010/019952 A2 | 2/2010 |
| WO | 2010/059315 A1 | 5/2010 |
| WO | 2011/022727 A2 | 2/2011 |
| WO | 2011/047180 A1 | 4/2011 |
| WO | 2011/112953 A2 | 9/2011 |
| WO | WO2011/112953 A2 * | 9/2011 |
| WO | 2012/019952 A1 | 2/2012 |
| WO | 2012/125573 A2 | 9/2012 |
| WO | 2012145507 A2 | 10/2012 |
| WO | 2012/154587 A2 | 11/2012 |
| WO | 2012/177440 A1 | 12/2012 |
| WO | 2013/023043 A2 | 2/2013 |
| WO | 2013/152034 A1 | 10/2013 |
| WO | 2015/130554 A2 | 9/2015 |

OTHER PUBLICATIONS

Bae et al., Breast Cancer Res. Treat, 2013; 139:741-50.*
Irvin & Carey, Eur. J. Cancer 2008; 44:2799-2805.*
E. A. Padlan, Adv Prot Chem 49:57-133; 1996.*
Li, Yu, et al., Expression and Activity of Carbonic Anhydrase IX is Associated With Metabolic Dysfunction in MDA-MB-231 Breast Cancer Cells, Cancer Investigation, 2009, vol. 27, pp. 613-623.
Thurber, Greg M. et al., "Antibody tumor penetration: Transport opposed by systemic and antigen-mediated clearance," Advanced Drug Delivery Reviews, vol. 60:1421-1434 (2008).
Tzahar, Eldad et al., "A Hierarchical Network of Interreceptor Interactions Determines Signal Transduction by Neu Differentiation Factor/Neuregulin and Epidermal Growth Factor," Molecular and Cellular Biology, vol. 16 (10):5276-5287 (1996).
Tzahar, Eldad et al., "ErbB-3 and ErbB-4 Function as the Respective Low and High Affinity Receptors of All Neu Differentiation Factor/Heregulin Isoforms," The Journal of Biological Chemistry, vol. 269(40):25226-25233 (1994).
Ullrich, Axel et al., "Signal Transduction by Receptors with Tyrosine Kinase Activity," Cell, vol. 61:203-212 (1990).
Vaidya, Pradeep et al., "Overexpression of Different Members of the Type 1 Growth Factor Receptor Family and Their Association with Cell Proliferation in Periampullary Carcinoma," Journal of Pathology, vol. 178:140-145 (1996).
Vajdos, Felix F. et al., "Comprehensive Functional Maps of the Antigen-binding Site of an Anti-ErbB2 Antibody Obtained with Shotgun Scanning Mutagenesis," J. Mol. Biol., vol. 320:415-428 (2002).

(56) References Cited

OTHER PUBLICATIONS

Voskoglou-Nomikos, Theodora et al., "Clinical Predictive Value of the in Vitro Cell Line, Human Xenograft, and Mouse Allograft Preclinical Cancer Models," Clinical Cancer Research, vol. 9:4227-4239 (2003).
Wainstein, Mark A. et al., "CWR22: Androgen-dependent Xenograft Model Derived from a Primary Human Prostatic Carcinoma," Cancer Research, vol. 54:6049-6052 (1994).
Wallasch, Christian et al., "Heregulin-dependent regulation of HER2/neu oncogenic signaling by heterodimerization with HER3," The EMBO Journal, vol. 14(17):4267-4275 (1995).
Ward, E. Sally et al., "Binding activities of a repertoire of single immunoglobulin variable domains secreted from *Escherichia coli*," Nature, vol. 341:544-546 (1989).
Wingens, Miriam et al., "Structural Analysis of an Epidermal Growth Factor/Transforming Growth Factor-a Chimera with Unique ErbB Binding Specificity," The Journal of Biological Chemistry, vol. 278(40):39114-39123 (2003).
Wu, Dianging et al., "Human Epidermal Growth Factor (EGF) Receptor Sequence Recognized by EGF Competitive Monoclonal Antibodies," The Journal of Biological Chemistry, vol. 264(29):17469-17475 (1989).
Wu, Herren et al., "Humanization of a Murine Monoclonal Antibody by Simultaneous Optimization of Framework and CDR Residues," J. Mol. Biol., vol. 294:151-162 (1999).
Yamamoto, Tadashi et al., "Similarity of protein encoded by the human c-erb-B-2 gene to epidermal growth factor receptor," Nature, vol. 319:230-234 (1986).
Ye, Dingwei et al., "Augmentation of a humanized Anti-HER2 mAb 4D6 induced growth inhibition by a human-mouse chimeric anti-EGF receptor mAb C225," Oncogene, vol. 18:731-738 (1999).
Zelada-Hedman, Moraima et al., "High Expression of the EGFR in Fibroadenomas Compared to Breast Carcinomas," Anticancer Research, vol. 14:1679-1688 (1994).
Zhang, Ke et al., "Transformation of NIH 3T3 Cells by HER3 or HER4 Receptors Requires the Presence of HER1 or HER2," The Journal of Biological Chemistry, vol. 271(7):3884-3890 (1996).
Invitation to Pay Additional Fees for Application No. PCT/US2008/002119, dated Oct. 7, 2008.
International Search Report and Written Opinion for Application No. PCT/US2008/002119, dated Dec. 3, 2008.
International Preliminary Report on Patentability for Application No. PCT/US2008/002119, dated May 18, 2009.
International Search Report for Application No. PCT/US2011/028129, 4 pages, dated Oct. 13, 2011.
International Preliminary Report on Patentability and Written Opinion for Application No. PCT/US2011/028129, 8 pages, dated Sep. 11, 2012.
International Search Report and Written Opinion for Application No. PCT/US2009/054051, dated May 4, 2010.
International Preliminary Report on Patentability for Application No. PCT/US2009/054051, dated Feb. 15, 2011.
Cleary, J.M.,"A Phase 1 Study of MM-121 (a fully human monoclonal antibody targeting the epidural growth factor receptor family member ErbB3) in Combination with Cetuximab and Irinotecan in Patients with Advanced Cancers," American Society of Clinical Oncology, 2014, Poster Presentation, 1 page.
Curley, M., et al., "MM-121/SAR256212, an anti-ErbB3 antibody, restores sensitivity to letrozole and delays the onset of resistance in an ER+ breast cancer model," Merrimack Pharmaceuticals & Sanofi, Apr. 1, 2013, Poster Presentation, pp. 1-22.
Curley, M., "MM-121, an anti-ErbB3 antibody, inhibits PI3K/AKT signaling and viability in platinum-resistant ovarian cells; and in primary ascites derived from chemo-resistant ovarian cancer patients," European Organisation for Research and Treatment of Cancer (EORTC), 2012,Poster No. 108, p. 1.
Denlinger, C.S., et al., "A Phase 1 Study of MM-121 in Combination with Multiple Anticancer Therapies in Patients with Advanced Solid Tumors," American Society of Clinical Oncology, 2013, Poster Presentation, 1 page.

Denlinger, C.S., et al., "Phase 1 Dose escalation Study of MM-121, a Fully Human Monoclonal Antibody to ErbB3, in Patients with Advanced Solid Tumors," American Association for Cancer Research (AACR) Annual meeting, 2011, 1 page.
Higgins, M., et al., "A Randomized, Double-Blind Phase II Trial of Exemestane+MM-121, monoclonal antibody targeting ErbB3,or placebo in Postmenopausal Women with Locally Advanced or Metastatic ER+/PR+,Her2-negative Breast Cancer," American Society of Clinical Oncology, 2014, Poster Presentation, 1 page.
Holmes. F., et al., "A Randomized, Phase 2 Trial of Preoperative MM-121 with Paclitazel in triple Negative (TNBC) and Hormone Receptor (HR) Positive, HER2-negative Breast Cancer," San Antonio Breast Cancer Symposium—Dec. 9-13, 2014, Poster Presentation, 1 page.
Jiang, N., et al., "Combined Treatment with HER3 Antibody MM-121/SAR 256212 and EGFR Antibody Cetuximab for Preclinical Models of Head and Neck Cancer," American Association for Cancer Research (AACR) Annual meeting, 2013, Emory University Poster, 1 page.
Liu, J. et al., "A Phase 1 Study of the anti-ErbB3 antibody MM-121 in combination with weekly paclitaxel in patients with advanced gynecological and breast cancers," European Society for Medical Oncology Annual Congress, Vienna, Austria, Sep. 28 to Oct. 2, 2012, Poster Presentation, 1 page.
Liu, J. et al., "A Phase 2 Randomized Open Label Study of MM-121, a Fully Human Monoclonal Antibody Targeting ErbB3, in Combination with Weekly Paclitaxel, Versus Weekly Paclitaxel Alone, in Patients with Platinum Resistant/Refractory Ovarian Cancers," American Society of Clinical Oncology, 2014, Poster Presentation, 1 page.
MacBeath, G. et al., A Meta-Analysis of Biomarkers in Three Randomized, Phase 2 Studies of MM-121, a Ligand-Blocking Anti-ErbB3 Antibody, in Patients with Ovarian, Lung and Breast Cancers, European Society for Medical Oncology (ESMO) Annual Meeting, 2014, Madrid Spain, Poster Presentation, 1 page.
Masson, K. et al., "The ErbB3-targeting antibody MM-121 (seribantumab) abrogates heregulin-driven resistance to multiple chemotherapies in preclinical models," European Association for Cancer Research (EACR) AACR Poster, Merrimack Pharmaceuticals, 2015, 1 page.
Masson, K. et al., "The ErbB3-targeting antibody MM-121 (seribantumab) abrogates heregulin-driven resistance to multiple chemotherapies in preclinical models," Abstract No. LB-243, Poster, American Association for Cancer Research (AACR) Annual meeting, 2015, 1 page.
Nie, L., et al., "High ErbB4/ErbB3 Ratio Attenuates Efficacy of Anti-ErbB3 Therapy," Abstract No. 677, European Association for Cancer Research (EACR) ErbB4 Poster, Merrimack Pharmaceuticals, 2015, 1 page.
Onsum, M., et al., "Prediction of xenograft response to MM-121, an anti-ErbB3 inhibitor, using computational modeling and measurements of five biomarkers," American Association for Cancer Research (AACR) Annual meeting, 2010, M. Onsum Biomarkers Poster, Abstract No. 3756, 1 page.
Sequist, L.V., et al., "A Randomized Phase 2 Trial of MM-121, a Fully Human Monoclonal Antibody Targeting ErbB3, in Combination with Erlotinib, in EGFR Wild-type NSCLC Patients," American Society of Clinical Oncology, 2014, Poster Presentation, 1 page.
Sequist, L.V., et al., "Targeting EGFR and ERBB3 in Lung Cancer Patients: Clinical Outcomes in a Phase 1 Trial of MM-121 in Combination with Erlotinib," American Society of Clinical Oncology, 2012, Poster Presentation, 1 page.
Wainszelbaum, Marisa et al., "In vitro studies of MM-121/SAR 256212, an anti-ErbB-3 antibody, in combination with erlotinib; in EGFR-wild-type NSCLC," AARC Meeting 2013, Poster 5464, p. 1.
Gamett, Daniel C. et al., "Heregulin-stimulated Signaling in Rat Pheochromocytoma Cells," The Journal of Biological Chemistry, vol. 270(32):19022-19027 (1995).
Gorgoulis, V. et al., "Molecular and immunohistochemical study of class I growth factor receptors in squamous cell lung carcinomas," Abstracts / Lung Cancer, vol. 14:381 (1996).
Gown, Allen M., "Current issues in ER and HER2 testing by IHC in breast cancer," Modern Pathology, vol. 21:S8-S15 (2008).

(56) References Cited

OTHER PUBLICATIONS

Grasso, Adam W. et al., "ErbB kinases and NDF signaling in human prostate cancer cells," Oncogene, vol. 15:2705-2716 (1997).

Gullick, W.J., "The c-erbB3/HER3 Receptor in Human Cancer," Cancer Surveys, vol. 27:339-349 (1996).

Guy, Pamela M. et al., "Insect cell-expressed p180erbB3 possesses an impaired tyrosine kinase activity," Proc. Natl. Acad. Sci. USA, vol. 91:8132-8136 (1994).

Harris, Lyndsay N. et al., "Molecular subtypes of breast cancer in reltaion to paclitaxel response and outcomes in women with metastatic disease: results from CALGB 9342," Breast Cancer Research, vol. 8(6):R66, 12 pages, doi:10.1186/bcr1622 (2006).

Heldin, Carl-Henrik, "Dimerization of Cell Surface Receptors in Signal Transduction," Cell, vol. 80:213-223 (1995).

Hellyer, Nathan J. et al., "Cloning of the rat ErbB3 cDNA and characterization of the recombinant protein," Gene, vol. 165:279-284 (1995).

Hofmann, Francesco et al., "Blocking insulin-like growth factor-I receptor as a strategy for targeting cancer," DDT, vol. 10(15):1041-1047 (2005).

Holm, Patrik et al., "Functional mapping and single chain construction of the anti-cytokeratin 8 monoclonal antibody TS1," Molecular Immunology, vol. 44:1075-1084 (2007).

Holmes, William E. et al., "Identification of Heregulin, a Specific Activator of p185erbB2," Science, vol. 256:1205-1210 (1992).

Holt, Lucy J. et al., "Domain antibodies: proteins for therapy," Trends in Biotechnology, Vo. 21(11):484-490 (2003).

Horan, Thomas et al., "Binding of Neu Differentiation Factor with the Extracellular Domain of Her2 and Her3," The Journal of Biological Chemistry, vol. 270(40):24604-24608 (1995).

Hsieh, AC et al., "Targeting HER proteins in cancer therapy and the role of the non-target HER3," British Journal of Cancer, vol. 97:453-457 (2007).

Htun Van Der Horst, Edward et al., "Anti-HER-3 MAbs Inhibit HER-3-Mediated Signaling in Breast Cancer Cell Lines Resistant to Anti-HER-2 Antibodies," Int. J. Cancer, vol. 115:519-527 (2005).

Issing, W.J. et al., "erbB-3, a third member of the erbB/epidermal growth factor receptor gene family: its expression in head and neck cancer cell lines," Eur. Arch. Otorhinolaryngol, vol. 250:392-395 (1993).

Jeschke, Margit et al., "Targeted Inhibition of Tumor-cell Growth by Recombinant Heregulin-toxin Fusion Proteins," Int. J. Cancer, vol. 60:730-739 (1995).

Jo, Sangmee Ahn et al., "Neuregulins are concentrated at nerve-muscle synapses and activate ACh-receptor gene expression," Nature, vol. 373:158-161 (1995).

Jones, Jennifer T. et al., "Binding specificities and affinities of egf domains for ErbB receptors," FEBS Letters, vol. 447:227-231 (1999).

Karunagaran, Devarajan et al., "ErbB-2 is a common auxiliary subunit of NDF and EGF receptors: implications for breast cancer," The EMBO Journal, vol. 15(2):254-264 (1996).

Kasprzyk, Philip G. et al., "Therapy of an Animal Model of Human Gastric Cancer Using a Combination of Anti-erbB-2 Monoclonal Antibodies," Cancer Research, vol. 52:2771-2776 (1992).

Katoh, Masaru et al., "c-erbB3 Gene Encodes Secreted as Well as Transmembrane Receptor Tyrosine Kinase," Biochemical and Biophysical Research Communications, vol. 192(3):1189-1197 (1993).

Kim, Hong-Hee et al., "Epidermal Growth Factor-dependent Association of Phosphatidylinositol 3-Kinase with the erbB3 Gene Product," The Journal of Biological Chemistry, vol. 269(40):24747-24755 (1994).

Kim, Hong-Hee et al., "Signal transduction by epidermal growth factor and heregulin via the kinase-deficient ErbB3 protein," Biochem. J., vol. 334:189-195 (1998).

Kinugasa, Yumi et al., "Neuroglycan C, a novel member of the neuregulin family," Biochemical and Biophysical Research Communications, vol. 321:1045-1049 (2004).

Kita, Yoshiko et al., "Bioactive Synthetic Peptide of NDF/Heregulin," Biochemical and Biophysical Research Communicatnions, vol. 210(2):441-451 (1995).

Kita, Yoshiko A. et al., "NDF/heregulin stimulates the phosphorylation of Her3/erbB3," FEBS Letters, vol. 349:139-143 (1994).

Klapper, Leah N. et al., "A subclass of tumor-inhibitory monoclonal antibodies to ErbB-2/HER2 blocks crosstalk with growth factor receptors," Oncogene, vol. 14:2099-2109 (1997).

Korabiowska, Monika et al., "Differential Expression of cerbB3 in Naevi and Malignant Melanomas," Anticancer Research, vol. 16:471-474 (1996).

Kraus, Matthias H. et al., "Demonstration of ligand-dependent signaling by the erbB-3 tyrosine kinase and its constitutive activation in human breast tumor cells," Proc. Natl. Acad. Sci. USA, vol. 90:290-2904 (1993).

Kraus, Matthias H. et al., "Isolation and characterization of ERBB3, a third member of the ERBB/epidermal growth factor receptor family: Evidence for overexpression in a dubset of human mammary tumors," Proc. Natl. Acad. Sci. USA, vol. 86:9193-9197 (1989).

Kraus, Matthias H. et al., "Overexpression of the EGF receptor-related proto-oncogene erbB-2 in human mammary tumor cell lines by different molecular mechanisms," The EMBO Journal, vol. 6(3):605-610 (1987).

Kumar, Sanjeev et al., "Molecular Cloning and Expression of the Fabs of Human Autoantibodies in *Escherichia coli*," The Journal of Biological Chemistry, vol. 275(45):35129-35136 (2000).

Lee, Hakjoo et al., "A Naturally Occurring Secreted Human ErbB3 Receptor Isoform Inhibits Heregulin-stimulated Activation of ErbB2, ErbB3, and ErbB4," Cancer Research, vol. 61:4467-4473 (2001).

Lee, Hakjoo et al., "Isolation and characterization of four alternate c-erbB3 transcripts expressed in ovarian carcinoma-derived cell lines and normal human tissues," Oncogene, vol. 6:3243-3252 (1998).

Lee-Hoeflich, Si Tuen et al., "A Central Role for HER3 in HER2-Amplified Breast Cancer: Implications for Targeted Therapy," Cancer Res., vol. 68(14):5878-5887 (2008).

Lemoine, Nicholas R. et al., "The erbB-3 Gene in Human Pancreatic Cancer," Journal of Pathology, vol. 168:269-273 (1992).

Levi, Allan D.O. et al., "The Influence of Heregulins on Human Schwann Cell Proliferation," The Journal of Neuroscience, vol. 15(2):1329-1340 (1995).

Lewis, Gail D. et al., "Growth Regulation of Human Breast and Ovarian Tumor Cells by Heregulin: Evidence for the Requirement of ErbB2 as a Critical Component in Mediating Heregulin Responsiveness," Cancer Research, vol. 56:1457-1465 (1996).

Little, M. et al., "Of mice and men: hybridoma and recombinant antibodies," Immunology Today, vol. 21(8):364-370 (2000).

Lu, Dan et al., "Complete Inhibition of Vascular Endothelial Growth Factor (VEGF) Activities with a Bifunctional Diabody Directed against Both VEGF Kinase Receptors, fms-like Tyrosine Kinase Receptor and Kinase Insert Domain-containing Receptor," Cancer Research, vol. 61:7002-7008 (2001).

MacCallum, Robert M. et al., "Antibody-antigen interactions: Contact Analysis and Binding Site Topography," J. Mol. Biol., vol. 262:732-745 (1996).

Marchionni, Mark A. et al., "Glial growth factors are alternatively spliced erbB2 ligands expressed in the nervous system," Nature, vol. 362:312-318 (1993).

Marte, Barbara M. et al., "Neu Differentiation Factor/Heregulin Modulates Growth and Differentiation of HC11 Mammary Epithelial Cells," Molecular Endocrinology, vol. 9:14-23 (1995).

McCall, Adrian M. et al., "Increasing the Affinity for Tumor Antigen Enhances Bispecific Antibody Cytotoxicity," The Journal of Immunology, vol. 166:6112-6117 (2001).

Morrissey, Thomas K. et al., "Axon-induced mitogenesis of human Schwann cell involves heregulin and p185erbB2," Proc. Natl. Acad. Sci. USA, vol. 92:1431-1435 (1995).

(56) References Cited

OTHER PUBLICATIONS

Moscosco, Lisa M. et al., "Synapse-Associated Expression of an Acetylcholine Receptor-Inducing Protein, ARIA/ Heregulin, and Its Putative Receptors, ErbB2 and ErbB3, in Developing Mammalian Muscle," Developmental Biology, vol. 172:158-169 (1995).
Myers, Russell B. et al., "Expression of p160erbB-3 and p185erbB-2 in Prostatic Intraepithelial Neoplasia and Prostatic Adenocarcinoma," Journal of the National Cancer Institute, vol. 86(15):1140-1145 (1994).
Naidu, R. et al., "Expression of c-erbB3 protein in primary breast carcinomas," British Journal of Cancer, vol. 78 (10):1385-1390 (1998).
Nie, Lin et al., "Efficacy of MM121 in ER+ and triple negative breast cancer studies," Proceedings of the American Association for Cancer Research, vol. 51:436, Poster Presentation No. 1806 (2010).
Nielsen, Ulrik B. et al., "Targeting of Bivalent Anti-ErbB2 Diabody Antibody Fragments to Tumor Cells Is Independent of the Intrinsic Antibody Affinity," Cancer Research, vol. 60:6434-6440 (2000).
Oikawa, Tetsuro et al., "Frequent Expression of Genes for Receptor Tyrosine Kinases and Their Ligands in Human Pancreatic Cancer Cells," International Journal of Pancreatology, vol. 18(1):15-23 (1995).
Orr-Urtreger, Avi et al., "Neural expression and chromosomal mapping of Neu differentiation factor to 8p12-p21," Proc. Natl. Acad. Sci. USA, vol. 90:1867-1871 (1993).
Peles, Elior et al., "Cell-type specific interaction of Neu differentiation factor (NDF/heregulin) with Neu/HER-2 suggests complex ligand-receptor relationships," The EMBO Journal, vol. 12(3):961-971 (1993).
Pierce, Jacalyn H. et al., "Signal Transduction Through the EGF Receptor Transfected in IL-3-Dependent Hematopoietic Cells," Science, vol. 239:628-631 (1988).
Pinkas-Kramarski, Ronit et al., "Diversification of Neu differentiation factor and epidermal growth factor signaling by combinatorial receptor interactions," The EMBO Journal, vol. 15(10):2452-2467 (1996).
Pinkas-Kramarski, Ronit et al., "Neu Differentiation Factor/Neuregulin Isoforms Activate Distinct Receptor Combinations," The Journal of Biological Chemistry, vol. 271(32):19029-19032 (1996).
Pinkas-Kramarski, Ronit et al., "The oncogenic ErbB-2/ErbB-3 heterdimer is a surrogate receptor of the epidermal growth factor and betacellulin," Oncogene, vol. 16:1249-1258 (1998).
Plowman, Gregory D. et al., "Heregulin induces tyrosine phosphorylation of HER4/p180erbB4," Nature, vol. 366:473-475 (1993).
Plowman, Gregory D. et al., "Ligand-specific activation of HER4/p180erbB4, a fourth member of the epidermal growth factor receptor family," Proc. Natl. Acad. Sci. USA, vol. 90:1746-1750 (1993).
Plowman, Gregory D. et al., "Molecular cloning and expression of an additional epidermal growth factor receptor-related gene," Proc. Natl. Acad. Sci. USA, vol. 87:4905-4909 (1990).
Poller, D.N. et al., "Production and Characterization of a Polyclonal Antibody to the c-erbB-3 Protein: Examination of c-erbB-3 Protein Expression in Adenocarcinomas," Journal of Pathology, vol. 168:275-280 (1992).
Presta, Leonard, "Antibody engineering for therapeutics," Current Opinion in Structural Biology, vol. 13:519-525 (2003).
Prigent, S.A. et al., "Expression of the c-erbB-3 protein in normal human adult and fetal tissues," Oncogene, vol. 7:1273-1278 (1992).
Prigent, Sally A. et al., "The Type 1 (EGFR-related) Family of Growth Factor Receptors and Their Ligands," Progress in Growth Factor Research, vol. 4:1-24 (1992).
Quinn, C.M. et al., "c-erbB-3 protein expression in human breast cancer: comparison with othe tumour variables and survival," Histopathology, vol. 25:247-252 (1994).
Rajkumar, T. et al., "A monoclonal antibody to the human c-erbB3 protein stimulates the anchorage-independent growth of breast cancer cell lines," Br. J. Cancer, vol. 70:459-465 (1994).
Rajkumar, Thangarajan et al., "Experssion of the C-erbB-3 Protein in Gastrointestinal Tract Tumours Determined by Monoclonal Antibody RTJ1," Journal of Pathology, vol. 170:271-278 (1993).
Rajkumar, T. et al., "Prevelance of c-erbB3 expression in squamous cell carcinomas of the cervix as determined by the monoclonal antibody RTJ2," International Journal of Oncology, vol. 6:105-109 (1995).
Rajkumar, Thangarajan et al., "The Type I growth factor receptors in human breast cancer," Breast Cancer Research and Treatment, vol. 29:3-9 (1994).
Ross, Jeffrey S. et al., "The HER-2/neu Oncogene in Breast Cancer: Prognostic Factor, Predictive Factor, and Target for Therapy," The Oncologist, vol. 3:237-252 (1998).
Rouzier, Roman et al., "Breast Cancer Molecular Subtypes Respond Differently to Preoperative Chemotherapy," Clin. Cancer Res., vol. 11(16):5678-5685 (2005).
Rudikoff, Stuart et al., "Single amino acid substitution altering antigen-binding specificity," Proc. Natl. Acad. Sci. USA, vol. 79:1979-1983 (1982).
Rudnick, Stephen I. et al., "Affinity and Avidity in Antibody-Based Tumor Targeting," Cancer Biotherapy and Radiopharmaceuticals, vol. 24(2):155-161 (2009).
Sadick, Michael D. et al., "Analysis of Heregulin-Induced ErbB2 Phosphorylation wtih a High-Throughput Kinase Receptor Activation Enzyme-Linked Immunosorbent Assay," Analytical Biochemistry, vol. 235:207-214 (1996).
Salomon, David S. et al., "Epidermal growth factor-related peptides and their receptors in human malignancies," Critical Reviews in Oncology/Hematology, vol. 19:183-232 (1995).
Sanidas, E.E. et al., "Expression of the c-erbB-3 Gene Product in Gastric Cancer," Int. J. Cancer, vol. 54:935-940 (1993).
Schaefer, Karl-Ludwig et al., "Constitutive Activation of Neuregulin/ERBB3 Signaling Pathway in Clear Cell Sarcoma of Soft Tissue," Neoplasia, vol. 8(7):613-622 (2006).
Schaefer, Karl-Ludwig et al., "Expression Profiling of t(12;22) Positive Clear Cell Sarcoma of Soft Tissue Cell Lines Reveals Characteristic Up-Regulation of Potential New Marker Genes Including ERBB3," Cancer Research, vol. 64:3395-3405 (2004).
Schmidt, M. et al., "Targeted inhibition of tumour cell growth by a bispecific single-chain toxin containing an antibody domain and TGFa," British Journal of Cancer, vol. 74:853-862 (1996).
Schneider, Bryan P. et al., "Triple-Negative Breast Cancer: Risk Factors to Potential Targets," Clin. Cancer Res., vol. 14(24):8010-8018 (2008).
Schoeberl, Birgit et al., "An ErbB3 Antibody, MM-121, Is Active in Cancers with Ligand-Dependent Activation," Cancer Res., vol. 70(6):2485-2494 (2010).
Schoeberl, Birgit et al., "Computational modeling and simulation lead to the development of MM-121 a human monoclonal antibody ErbB3 antagonist," 99th AACR Annual Meeting, Poster Presentation Abstract No. 1638 (2008).
Schoeberl, Birgit et al., "MM-121:a human monoclonal antibody ErbB3 antagonist," 99th AACR Annual Meeting, Poster Presentation Abstract No. 3974 (2008).
Semba, Kentaro et al., "A v-erbB-related protooncogene, c-erbB-2, is distinct from the c-erbB-1/epidermal growth factor-receptor gene and is amplified in a human salivary gland adenocarcinoma," Proc. Natl. Acad. Sci. USA, vol. 82:6497-6501 (1985).
Shintani, Satoru et al., "Expression of C-erbB Family Gene Products in Adenoid Cystic Carcinoma of Salivary Glands: An Immunohistochemical Study," Anticancer Research, vol. 15:2623-2626 (1995).
Shintani, Satoru et al., "Prognostic significance of ERRB3 overexpression in oral squamous cell carcinoma," Cancer Letters, vol. 95:79-83 (1995).
Simpson, Barbara J.B. et al., "c-erbB Growth-factor-receptor Proteins in Ovarian Tumours," Int. J. Cancer (Pred. Oncol.), vol. 64:202-206 (1995).
Simpson, BJB et al., "c-erbB-3 protein expression in ovarian tumours," British Journal of Cancer, vol. 71:758-762 (1995).
Singer, Elizabeth et al., "Identification of a Heregulin Binding Site in HER3 Extracellular Domain," The Journal of Biological Chemistry, vol. 276(47):44266-44274 (2001).

(56) References Cited

OTHER PUBLICATIONS

Skinner, Ann et al., "Transcriptional regulation of the c-erbB-3 gene in human breast carcinoma cell lines," Oncogene, vol. 8:3393-3401 (1993).
Slamon, Dennis J. et al., "Human Breast Cancer: Correlation of Relapse and Survival with Amplification of the HER-2/neu Oncogene," Science, vol. 235:177-182 (1987).
Slamon, Dennis J. et al., "Studies of the HER-2/neu Proto-oncogene in Human Breast and Ovarian Cancer," Science, vol. 244:707-712 (1989).
Sliwkowski, Mark X. et al., "Coexpression of erbB2 and erbB3 Proteins Reconstitutes a High Affinity Receptor for Heregulin," The Journal of Biological Chemistry, vol. 269(2):14661-14665 (1994).
Smith, B.L. et al., "The efficacy of Herceptin therapies is influenced by the expression of other erbB receptors, their ligands and the activation of downstream signalling proteins," British Journal of Cancer, vol. 91:1190-1194 (2004).
Smith-Gill, Sandra J. et al., "Contributions of Immunoglobulin Heavy and Light Chains to Antibody Specificity for Lysozyme and Two Haptens," The Journal of Immunology, vol. 139:4135-4144 (1987).
Soltoff, Stephen P. et al., "ErbB3 Is Involved in Activation of Phosphatidylinositol 3-Kinase by Epidermal Growth Factor," Molecular and Cellular Biology, vol. 14(6):3550-3558 (1994).
Song, Mi-Kyung et al., "Light Chain of Natural Antibody Plays a Dominant Role in Protein Antigen Binding," Biochemical and Biophysical Research Communications, vol. 268:390-394 (2000).
Surmacz, Eva, "Growth factor receptors as therapeutic targets: strategies to inhibit the insulin-like growth factor I receptor," Oncogene, vol. 22:6589-6597 (2003).
Aaronson, S.A. et al., "Growth factor-regulated pathways in epithelial cell proliferation," Am. Rev. Respir. Dis., vol. 142(6 pt. 2):S7-S10 (1990).
Adapt, The Peterson Institute for Cancer Research, Probesets for ErbB1, 4 pages (2013).
Adapt, The Peterson Institute for Cancer Research, Probesets for ErbB2, 3 pages (2013).
Adapt, The Peterson Institute for Cancer Research, Probesets for ErbB3, 3 pages (2013).
Adapt, The Peterson Institute for Cancer Research, Probesets for Betacellulin (BTC), 2 pages (2013).
Adapt, The Peterson Institute for Cancer Research, Probesets for neuregulin (NRG1), 14 pages (2013).
Alberts, Bruce et al., Molecular Biology of the Cell, Third Edition, Garland Publishing, Inc., New York, pp. 897-899 (1994).
Alimandi, Maurizio et al., "Cooperative signaling of ErbB3 and ErbB2 in neoplastic transformation and human mammary carcinomas," Oncogene, vol. 10:1813-1821 (1995).
Alimandi, Maurizio et al., "Epidermal growth factor and betacellulin mediate signal transduction through co-expressed ErbB2 adn ErbB3 receptors," The EMBO Journal, vol. 16(18):5608-5617 (1997).
ATCC, "AdrR," retrieved online at: http://www.atcc.org/ATCCAdvancedCatalogSearch/AllCollectionSearch/tabid/454/Default.aspx (2011).
Balint, Robert F. et al., "Antibody engineering by parsimonious mutagenesis," Gene, vol. 137:109-118 (1993).
Baselga, Jose et al., "Novel anticancer targets: revisiting ERBB2 and discovering ERBB3," Nature Reviews Cancer, vol. 9(7):463-475 (2009).
Becerril, Baltazar et al., "Toward Selection of Internalizing Antibodies from Phage Libraries," Biochemical and Biophysical Research Communications, vol. 255:386-393 (1999).
Beckman, Robert A. et al., "Antibody Constructs in Cancer Therapy, Protein Engineering Strategies to Improve Exposure in Solid Tumors," Cancer, vol. 109:170-179 (2007).
Beerli, Roger R. et al., "Neu Differentiation Factor Activation of ErbB-3 and ErbB-4 Is Cell Specific and Displays a Differential Requirement for ErbB-2," Molecular and Cellular Biology, vol. 15(12):6496-6505 (1995).

Bodey, Bela et al., "Immunophenotypically Varied Cell Subpopulations in Primary and Metastatic Human Melanomas. Monoclonal Antibodies for Diagnosis, Detection of Neoplastic Progression and Receptor Directed Immunotherapy," Anticancer Research, vol. 16:517-532 (1996).
Bortoletto, Nicola et al., "Optimizing anti-CD3 affinity for effective T cell targeting against tumor cells," Eur. J. Immunol., vol. 32:3102-3107 (2002).
Bostwick, David G., "c-erbB-2 Oncogene Expression in Prostatic Intraepithelial Neoplasia: Mounting Evidence for a Precursor Role," Journal of the National Cancer Institute, vol. 86(15):1108-1110 (1994).
Brand, Francois-Xavier et al., "Prospect for anti-HER2 Receptor Therapy in Breast Cancer," Anticancer Research, vol. 26:463-470 (2006).
Brotherick, Ian et al., "A flow cytometric study of c-erbB-3 expression in breast cancer," Cancer Immunol. Immunother, vol. 41:280-286 (1995).
Campbell, Marcia R. et al., "HER3 Comes of Age: New Insights into the Functions and Role in Signaling, Tumor Biology, and Cancer Therapy," Clin. Cancer Res., vol. 16(5):1373-1383 (2010).
Carraway, Kermit L. III et al., "A Neu Acquaintance for ErbB3 and ErbB4: A Role for the Receptor Heterodimerization in Growth Signaling," Cell, vol. 78:5-8 (1994).
Carraway, Kermit L. III et al., "Heregulin Stimulates Mitogenesis and Phosphatidylinositol 3-Kinase in Mouse Fibroblasts Transfected with erbB2/neu and erbB3," The Journal of Biological Chemistry, vol. 270(13):7111-7116 (1995).
Carraway, Kermit L. III et al., "The erbB3 Gene Product Is a Receptor for Heregulin," The Journal of Biological Chemistry, vol. 269(19):14303-14306 (1994).
Casset, Florence et al., "A peptide mimetic of an anti-CD4 monoclonal antibody by rational design," Biochemical and Biophysical Research Communications, vol. 307:198-205 (2003).
Cespedes, Maria Virtudes et al., "Mouse models in oncogenesis and cancer therapy," Clin. Transl. Oncol., vol. 8 (5):318-329 (2006).
Chan, Andrew C. et al., "Therapeutic antibodies for autoimmunity and inflammation," Nature Reviews Immunology, vol. 10:301-316 (2010).
Chen, Xiaomei et al., "An Immunological Approach Reveals Biological Differences between the Two NDF/Heregulin Receptors, ErbB-3 and ErbB-4," The Journal of Biological Chemistry, vol. 271(13):7620-7629 (1996).
Chen, Yvonne et al., "Selection and Analysis of an Optimized Anti-VEGF Antibody: Crystal Structure of an Affinity-matured Fab in Complex with Antigen," J. Mol. Biol., vol. 293:865-881 (1999).
Ciardiello, Fortunato et al., "Differential expression of epidermal growth factor-related proteins in human colorectal tumors," Proc. Natl. Acad. Sci. USA, vol. 88:7792-7796 (1991).
Davies, Jullian et al., "Affinity improvement of single antibody VH domains: residues in all three hypervariable regions affect antigen binding," Immunotechnology, vol. 2:169-179 (1996).
Dennis, Carina, "Off by a whisker," Nature, vol. 442:739-741 (2006).
De Pascalis, Roberto et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, vol. 169:3076-3084 (2002).
Di Fiore, Pier Paolo et al., "Mechanisms involving an expanding erbB/EGF receptor family of tyrosine kinases in human neoplasia," Genes, Oncogenes, and Hormones, Robert B. Dickson, Ed., Kluwer Academic Publishers, pp. 139-160 (1992).
Dorvillius, Mylene et al., "Targeting of Human Breast Cancer by a Bispecific Antibody Directed against Two Tumour-Associated Antigens: ErbB-2 and Carcinoembryonic Antigen," Tumor Biol., vol. 23:337-347 (2002).
Drebin, Jeffrey A. et al., "Monoclonal antibodies reactive with distinct domains of the neu oncogene-encoded p185 molecule exert synergistic anti-tumor effects in vivo," Oncogene, vol. 2:273-277 (1988).

(56) References Cited

OTHER PUBLICATIONS

Eccles, Suzanne A. et al., "Significance of the c-erbB Family of Receptor Tyrosine Kinases in Metastatic Cancer and Their Potential as Targets for Immunotherapy," Invasion Metastasis, vol. 14:337-348 (1995).
Erjala, Kaisa et al., "Signaling via ErbB2 and ErbB3 Associates with Resistance and Epidermal Growth Factor Receptor (EGFR) Amplification with Sensitivity to EGFR Inhibitor Gefitinib in Head and Neck Squamous Cell Carcinoma Cells," Clin. Cancer Res., vol. 12(13):4103-4111 (2006).
Esteva, Francisco J. et al., "Expression of erbB/HER Receptors, Heregulin and P38 in Primary Breast Cancer using Quantitative Immunohistochemistry," Pathology Oncology Research, vol. 7(3):171-177 (2001).
Ethier, Stephen P. et al., "erbB Family Receptor Expression and Growth Regulation in a Newly Isolated Human Breast Cancer Cell Line," Cancer Research, vol. 56:899-907 (1996).
Faksvag, Dagny R. et al., "Expression of c-erbB-3 and c-erbB-4 Proteins in Papillary Thyroid Carcinomas," Cancer Research, vol. 56:1184-1188 (1996).
Fendly, Brian M. et al., "Characterization of Murine Monoclonal Antibodies Reactive to Either the Human Epidermal Growth Factor Receptor or HER2/neu Gene Product," Cancer Research, vol. 50:1550-1558 (1990).
Fiddes, Rodney J. et al., "Heregulin (HRG)-induced Mitogenic Signaling and Cytotoxic Activity of a HRG/PE40 Ligand Toxin in Human Breast Cancer Cells," Cell Growth & Differentiation, vol. 6:1567-1577 (1995).
Fitzpatrick, V. Danial et al., "Formation of a high affinity heregulin binding site using the soluble extracellular domains of ErbB2 with ErbB3 or ErbB4," FEBS Letters, vol. 431:102-106 (1998).
Foley, John et al., "EGFR Signaling in Breast Cancer: Bad to the Bone," Semin. Cell. Dev. Biol., vol. 21(9):951-960 (2010).
Francois, Christine et al., "Antibodies directed at mouse IL-2-R a and b chains act in synergy to abolish T-cell proliferation in vitro and delayed type hypersensitivity reaction in vivo," Transpl. Int., vol. 9:46-50 (1996).
Friess, Helmut et al., "Enhanced erbB-3 Expression in Human Pancreatic Cancer Correlates with Tumor Progression," Clinical Cancer Research, vol. 1:1413-1420 (1995).
Friess, H. et al., "Pancreatic cancer: the potential clinical relevance of alterations in growth factors and their receptors," J. Mol. Med., vol. 74:35-42 (1996).
Fuchs, C.S., "Gastric Carcinoma," The New England Journal of Medicine, vol. 333(21):1426-1428 (1995).
Fujimori, Kenji et al., "A Modeling Analysis of Monoclonal Antibody Percolation Through Tumors: A Binding-Site Barrier," J. Nucl. Med., vol. 31:1191-1198 (1990).
Baselga, Jose et al., "Phase II Trial of Pertuzumab and Trastuzumab in Patients With Human Epidermal Growth actor Receptor 2-Positive Metastatic Breast Cancer That Progressed During Prior Trastuzumab Therapy," Journal of Clinical Oncology, vol. 28(7):1138-1144 (2010).
Brodie, Angela et al., "Adaptive changes result in activation of alternative signaling pathways and acquisition of resistance to aromatase inhibitors," Clin. Cancer Res., vol. 17(13):4208-4213 (2011).
Brorson, Kurt et al., "Mutational Analysis of Avidity and Fine Specificity of Anti-Levan Antibodies," The Journal of Immunology, vol. 163:6694-6701 (1999).
Brown, McKay et al., "Tolerance to Single, but Not Multiple, Amino Acid Replacements in Antibody VH CDR2," The Journal of Immunology, vol. 156:3285-3291 (1996).
Brummell, David A. et al., "Probing the Combining Site of an Anti-Carbohydrate Antibody by Saturation-Mutagenesis: Role of the Heavy-Chain CDR3 Residues," Biochemistry, vol. 32:1180-1187 (1993).
Burks, Elizabeth A. et al., "In vitro scanning saturation mutagenesis of an antibody binding pocket," Proc. Natl. Acad. Sci. USA, vol. 94:412-417 (1997).

Cicenas, J. et al, "Phosphorylation of tyrosine 1248-ERBB2 measured by chemiluminescence-linked immunoassay is an independent predictor of poor prognosis in primary breast cancer patients," European J Cancer, vol. 42, pp. 636-645(2006).
Colman, P.M., "Effects of amino acid sequence changes on antibody-antigen interactions," Research in Immunology, vol. 145:33-36 (1994).
Denlinger, C.S. et al., "A phase 1/11 and pharmacologic study of MM-111 in patients with advanced, refractory HER2-positive (HER2+) cancers," J. Clin. Oncol., vol. 28(15s), 2010 ASCO Annual Meeting, Abstract No. TPS169, 4 pages (2010).
Dufner, Patrick et al., "Harnessing phage and ribosome display for antibody optimisation," Trends in Biotechnology, vol. 24(11):523-529 (2006).
Engelman, Jeffrey A. et al., "MET Amplification Leads to Gefitinib Resistance in Lung Cancer by Activating ERBB3 Signaling," Science, vol. 316:1039-1043 (2007).
European Search Report and Written Opinion for Application No. 13180584.8, 14 pages, dated Jun. 13, 2014.
Excerpt Wikipedia re Cetuximab, accessed Oct. 12, 2015.
Frogne, Thomas et al., "Activation of ErbB3, EGFR and Erk is essential for growth of human breast cancer cell lines with acquired resistance to fulvestrant," Breast Cancer Res. Treat., vol. 114(2):263-275 (2009).
Gasparini, G. et al., "Randomized phase II trial of weekly paclitaxelalone verus trastuzumab plus weekly paclitaxel as; first-line therapy of patients with Her-2 positive advanced breast cancer," Breast Cancer Res. Treat., vol. 101, pp. 355-365 (2007).
Hamburger, Anne W. et al., "The Role of ErbB3 and its Binding Partners in Breast Cancer Progression and Resistance to Hormone and Tyrosine Kinase Directed Therapies," J. Mammary Gland Biol. Neoplasia, vol. 13 (2):225-233 (2008).
Harms, Brian D. et al., "Application of computational modeling to guide the development of MM-111, a bispecific antibody targeting ErbB3 in ErbB2 overexpressing tumors," 2009 AACR Annual Meeting, Abstract No. 3298, 1 page (2009).
Harris, L.N et al., "Induction of sensitivity to doxorubicin and etoposide by transfection of MCF-7 breast cancer cells with heregulin beta-2," Clinical Cancer Research, 1998, vol. 4, pp. 1005-1012.
Holbro, Thomas et al., "The ErbB2/ErbB3 heterodimer functions as an oncogenic unit: ErbB2 requires ErbB3 to drive breast tumor cell proliferation," PNAS, vol. 100(15):8933-8938 (2003).
Huhalov, Alexandra et al., "MM-111: A novel ErbB3 antagonist with potent antitumor activity in ErbB2 over-expressing malignancies," 2009 MCR Annual Meeting, Abstract No. 5472, 2 pages (2009.
Information Disclosure Submission concerning Agreement between Dyax Corporation and Merrimack Pharmaceuticals, Jun. 30, 2010.
International Preliminary Report on Patentability and Written Opinion for Application No. PCT/US2012/042164, 8 pages, dated Mar. 25, 2014.
International Preliminary Report on Patentability for Application No. PCT/US2012/028792, 15 pages, dated Sep. 17, 2013.
International Search Report and Written Opinion, PCT/US2014/072594, dated Jun. 29, 2015, 18 pages.
International Search Report for Application No. PCT/US2012/028792, 7 pages, dated Nov. 8, 2012.
Jang, Y.-J. et al., "The structural basis for DNA binding by an anti-DNA autoantibody," Molecular Immunology, vol. 35:1207-1217 (1998).
Konecny, GE et al., "Activity of the dual kinase inhibitor lapatinib (GW572016) against HER-2-overexpressing and trastuzumab-treated breast cancer cells," Cancer Research, vol. 66, p. 1630-1639 (2006).
Lal, P. et al., "Correlation of HER-2 Status With Estrogen and Progesterone Receptors and Histologic Features in 3,655 Invasive Breast Carcinomas," American Journal of Clinical Pathology, vol. 123, pp. 541-546 (2005).
Lederman, Seth et al., "A Single Amino Acid Substitution in a Common African Allele of the CD4 Molecule Ablates Binding of the Monoclonal Antibody, OKT4," Molecular Immunology, vol. 28(11):1171-1181 (1991).

(56) References Cited

OTHER PUBLICATIONS

Lenz, H.J., "Management and Preparedness for Infusion and Hypersensitivity Reactions," The Oncologist, vol. 12, pp. 601-609, (2007).
Li, Choh Hao et al., "Beta-Endorphin omission analogs: Dissociation of immunoreactivity from other biological activities," Proc. Natl. Acad. Sci. USA, vol. 77(6):3211-3214 (1980).
Liu, B.et al., "Downregulation of erbB3 abrogates erbB2-mediated tamoxifen resistance in breast cancer cells," Int J Cancer, vol. 120, pp. 1874-1882 (2007).
Liu, Bolin et al., "Estrogenic Promotion of ErbB2 Tyrosine Kinase Activity in Mammary Tumor Cells Requires Activation of ErbB3 Signaling," Mol. Cancer Res., vol. 7(11):1882-1892 (2009).
Markman, M. et al., "Phase II trial of weekly paclitaxel (80 mg/m2) in platinum and paclitaxel-resistant ovarian and primary peritoneal cancers: a gynecologic oncology group study," Gyncol. Oncol., vol. 101, pp. 436-440 (2006).
McDonagh, Charlotte E et al., "Antitumor Activity of a Novel Bispecific Antibody That Targets the ErbB2/ErbB3 Oncogenic Unit and Inhibits Heregulin-Induced Activation of ErbB3," Mol. Cancer Ther., vol. 11(3):582-593 (2012).
Musgrove, Elizabeth A. et al., "Biological determinants of endocrine resistance in breast cancer," Nature Reviews Cancer, vol. 9:631-643 (2009).
Neve, et al, "A collection of breast cancer cell lines for the study of functionally distinct cancer subtypes" Cancer Cell, vol. 10(6):515-527 (2000).
Notice of Opposition to a European Patent for Patent No. EP 2318548, 7 pages, dated Jul. 21, 2014.
Notice of Opposition, European Application No. EP11730112.7, dated Oct. 13, 2015, pp. 1-21.
Opponents Written SubmissionSummons to Attend Oral Proceedings,European Patent for Patent No. EP 2318548, 24 pages, dated Jan. 11, 2016.
Perez, E.,"Paclitaxel in breast cancer," The Oncologist, 3(6), pp. 373-389 (1998).
Prat, A. et al., "The role of hormonal therapy in the management of hormonal-receptor-positive breast cancer with co-expression of HER2," Nature Clinical Practice Oncology vol. 5(9), pp. 531-542 (2008).
Sabnis, G. et al., "Trastuzumab Reverses Letrozole Resistance and Amplifies the Sensitivity of Breast Cancer Cells to Estrogen," Cancer Research, vol. 69, pp. 1416-1428 (abstract) (2009).
Sak, M. et al., "Pertuzuman counteracts the inhibitory effect of ErbB2 on degradation of ErbB3," Carcinogenesis, vol. 34(9), pp. 2031-2038 (2013).
Scartozzi, M. et al., "The Role of HER-3 Expression in the Predication of Clinical Outcome for Advanced Colorectal Cancer Patients Receiving Irinotecan and Cetuximab," The Oncologist, vol. 16, pp. 53-60 (2011).
Schoeberl, B. et al., "Therapeutically targeting ErbB3: A key node in ligand-induced activation of the ErbB receptor-PI3K axis," Science Signaling, American Association for the Advancement of Science, vol. 2 (77), pp. 1-14 (2009).
Siddiqui, S. et al., "Pre-analytic variables and phospho-specific antibodies: the Achilles heel of immunohistochemistry," Breast Cancer Research, vol. 12(113, pp. 1-2, (2010).
Sonne-Hansen, Katrine et al., "Breast cancer cells can switch between estrogen receptor alpha and ErbB signaling and combined treatment against both signaling pathways postpones development of resistance," Breast Cancer Res. Treat., vol. 121:601-613 (2010).
Wikipedia entry "Paclitaxel", English, accessed Aug. 13, 2015.
U.S. Appl. No. 14/965,301, filed Dec. 10, 2015, Bambang Adiwijaya.
U.S. Appl. No. 14/004,598, Sep. 14, 2015.
U.S. Appl. No. 14/130,058, Dec. 4, 2015.
U.S. Appl. No. 14/181,334, Oct. 27, 2015.
U.S. Appl. No. 14/967,158, filed Dec. 11, 2015, Gavin MacBeath.
U.S. Appl. No. 15/156,603, filed May 17, 2016, Bambang Adiwijaya.
U.S. Appl. No. 15/156,262, filed May 16, 2016, Bambang Adiwijaya.
U.S. Appl. No. 14/181,334, Feb. 19, 2016.
U.S. Appl. No. 14/965,301, Mar. 28, 2016.
BES. C. et al., "Mapping the paratope of anti-CD4 recombinant Fab 13B8.2 by combining parallel peptide synthesis and site-directed mutagenesis," Journal of Biological Chemistry, vol. 278 (16,18):14265-14273 (2003).
Board, RE, et al., "Multiplexed assays for detection of mutations in PIK3CA," Clin. Chem., vol. 54(4):757-760 (2008).
Burenkova, O. et al., "In vivo effect of combination therapy. An anti ErbB3 antibody, MM121, plus selected cancer therapies," Proceedings of the American Association for Cancer Research, Annual Meeting, (Apr. 18-22, 2009) Denver CO, 2 pages, Abstract 1243.
Curley, MD et al., "Seribantumab, an Anti-ERBB3 Antibody, Delays the Onset of Resistance and Restores Sensitivity to Letrozole in an Estrogen Receptor-Positive Breast Cancer Model," Mol. Cancer Ther., vol. 14(11):1-11 (2015).
Fitzgerald, JB, et al.,"MM-141, an IGF-IR- and ErbB3-directed bispecific antibody, overcomes network adaptations that limit activity of IGF-IR inhibitors," Mol. Cancer. Ther., 13(2), 410-425 (2014).
Fontayne, A. et al., "Paratope and epitope mapping of the antithrombotic antibody 6B4 in complex with platelet glycoprotein 1b alpha," Journal of Biological Chemistry, vol. 282 (32):23517-23524 (2007).
Guddat, LW, et al., "Three-dimensional structure of human immunoglobulin with a hinge deletion," Proceedings of The National Academy of Sciences, National Academy of Sciences, US, vol. 90: 4271-4275 (1993).
Huse, et al., "Generation of a large combinatorial library of the immunoglobulin repertoire in phage lambda," Science 246: 1275-1281 (1989).
Janku, F., et al., "PIK3CA mutations in patients with advanced cancers treated with PI3K/AKT/mTOR axis inhibitors," Mol. Cancer Ther., 10(3): 558-565 (2011).
Kohler, G. et al., "Derivation of specific antibody-producing tissue culture and tumor lines by cell fusion," Eur. J. Immunol., vol. 6(7): 511-519 (1976).
Sequist, L. et al., "MM-121: A Human mAb to ErbB3," Santa Monica Lung Cancer Meeting Presentation, 14 pages, 2014.
Sheng, Q. et al., "An activated ErbB3/NRG1 autocrine loop supports in vivo proliferation in ovarian cancer cells," Cancer Cell, vol. 17(3):298-310 (2010).
Wang, S. et al., "Therapeutic Targeting of ErbB3 with MM-121/Sar256212 enhances antitumor activity of paclitaxel against erbB2-overexpressing breast cancer," Breast Cancer Research, vol. 15(5): R101 (2013).
Yarar, D. et al., "Heregulin-ErbB3-driven tumor growth persists in PI3 Kinase Mutant Cancer Cells," Mol. Cancer Ther., vol. 14(9):2072-2080 (2015).

\* cited by examiner

SEQUENCE LISTING

<160> NUMBER OF SEQ ID NOS: 41

<210> SEQ ID NO 1
<211> LENGTH: 119
<212> TYPE: PRT
<213> ORGANISM: Homo sapiens

<400> SEQUENCE: 1

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Val Met Ala Trp Val Arg Gln Ala Pro Gly Lys Gly Leu Glu Trp Val
        35                  40                  45

Ser Ser Ile Ser Ser Ser Gly Gly Trp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Leu Lys Met Ala Thr Ile Phe Asp Tyr Trp Gly Gln Gly
            100                 105                 110

Thr Leu Val Thr Val Ser Ser
        115
```

<210> SEQ ID NO 2
<211> LENGTH: 111
<212> TYPE: PRT
<213> ORGANISM: Homo sapiens

<400> SEQUENCE: 2

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Val Val Ser Trp Tyr Gln Gln His Pro Gly Lys Ala Pro Lys Leu
        35                  40                  45

Ile Ile Tyr Glu Val Ser Gln Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Cys Ser Tyr Ala Gly Ser
                85                  90                  95

Ser Ile Phe Val Ile Phe Gly Gly Gly Thr Lys Val Thr Val Leu
            100                 105                 110

<210> SEQ ID NO 3
<211> LENGTH: 5
<212> TYPE: PRT
<213> ORGANISM: Homo sapiens

<400> SEQUENCE: 3

His Tyr Val Met Ala
1               5

<210> SEQ ID NO 4
<211> LENGTH: 17
<212> TYPE: PRT
<213> ORGANISM: Homo sapiens

<400> SEQUENCE: 4

Ser Ile Ser Ser Ser Gly Gly Trp Thr Leu Tyr Ala Asp Ser Val Lys
1               5                   10                  15

Gly

<210> SEQ ID NO 5
<211> LENGTH: 10
<212> TYPE: PRT
<213> ORGANISM: Homo sapiens

<400> SEQUENCE: 5

Gly Leu Lys Met Ala Thr Ile Phe Asp Tyr
1               5                   10

<210> SEQ ID NO 6
<211> LENGTH: 14
<212> TYPE: PRT
<213> ORGANISM: Homo sapiens

<400> SEQUENCE: 6

Thr Gly Thr Ser Ser Asp Val Gly Ser Tyr Asn Val Val Ser
1               5                   10

<210> SEQ ID NO 7
<211> LENGTH: 7
<212> TYPE: PRT
<213> ORGANISM: Homo sapiens

<400> SEQUENCE: 7

Glu Val Ser Gln Arg Pro Ser
1               5

<210> SEQ ID NO 8
<211> LENGTH: 11
<212> TYPE: PRT
<213> ORGANISM: Homo sapiens

<400> SEQUENCE: 8

Cys Ser Tyr Ala Gly Ser Ser Ile Phe Val Ile
1               5                   10

<210> SEQ ID NO 9
<211> LENGTH: 118
<212> TYPE: PRT
<213> ORGANISM: Homo sapiens

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Asn Met Arg Trp Val Arg Gln Ala Pro Gly Lys Gly Leu Glu Trp Val
        35                  40                  45

Ser Val Ile Tyr Pro Ser Gly Ala Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Tyr Tyr Gly Met Asp Val Trp Gly Gln Gly Thr
            100                 105                 110

Leu Val Thr Val Ser Ser
        115

<210> SEQ ID NO 10
<211> LENGTH: 110
<212> TYPE: PRT
<213> ORGANISM: Homo sapiens

<400> SEQUENCE: 10

Gln Ser Val Leu Thr Gln Pro Pro Ser Ala Ser Gly Thr Pro Gly Gln
1               5                   10                  15

Arg Val Thr Ile Ser Cys Ser Gly Ser Asp Ser Asn Ile Gly Arg Asn
            20                  25                  30

Tyr Ile Tyr Trp Tyr Gln Gln Phe Pro Gly Thr Ala Pro Lys Leu Leu
        35                  40                  45

Ile Tyr Arg Asn Asn Gln Arg Pro Ser Gly Val Pro Asp Arg Ile Ser
    50                  55                  60

Gly Ser Lys Ser Gly Thr Ser Ala Ser Leu Ala Ile Ser Gly Leu Arg
65                  70                  75                  80

Ser Glu Asp Glu Ala Glu Tyr His Cys Gly Thr Trp Asp Asp Ser Leu
                85                  90                  95

Ser Gly Pro Val Phe Gly Gly Gly Thr Lys Leu Thr Val Leu
            100                 105                 110

<210> SEQ ID NO 11
<211> LENGTH: 5
<212> TYPE: PRT
<213> ORGANISM: Homo sapiens

```
<400> SEQUENCE: 11

Ala Tyr Asn Met Arg
1               5

<210> SEQ ID NO 12
<211> LENGTH: 17
<212> TYPE: PRT
<213> ORGANISM: Homo sapiens

<400> SEQUENCE: 12

Val Ile Tyr Pro Ser Gly Gly Ala Thr Arg Tyr Ala Asp Ser Val Lys
1               5                   10                  15

Gly

<210> SEQ ID NO 13
<211> LENGTH: 9
<212> TYPE: PRT
<213> ORGANISM: Homo sapiens

<400> SEQUENCE: 13

Gly Tyr Tyr Tyr Tyr Gly Met Asp Val
1               5

<210> SEQ ID NO 14
<211> LENGTH: 13
<212> TYPE: PRT
<213> ORGANISM: Homo sapiens

<400> SEQUENCE: 14

Ser Gly Ser Asp Ser Asn Ile Gly Arg Asn Tyr Ile Tyr
1               5                   10

<210> SEQ ID NO 15
<211> LENGTH: 7
<212> TYPE: PRT
<213> ORGANISM: Homo sapiens

<400> SEQUENCE: 15

Arg Asn Asn Gln Arg Pro Ser
1               5

<210> SEQ ID NO 16
<211> LENGTH: 11
<212> TYPE: PRT
<213> ORGANISM: Homo sapiens

<400> SEQUENCE: 16

Gly Thr Trp Asp Asp Ser Leu Ser Gly Pro Val
1               5                   10

<210> SEQ ID NO 17
<211> LENGTH: 122
<212> TYPE: PRT
<213> ORGANISM: Homo sapiens

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Gly Met Gly Trp Val Arg Gln Ala Pro Gly Lys Gly Leu Glu Trp Val
        35                  40                  45
```

```
Ser Tyr Ile Ser Pro Ser Gly Gly His Thr Lys Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Leu Glu Thr Gly Leu Leu Val Asp Ala Phe Asp Ile Trp
            100                 105                 110

Gly Gln Gly Thr Met Val Thr Val Ser Ser
            115                 120
```

<210> SEQ ID NO 18
<211> LENGTH: 106
<212> TYPE: PRT
<213> ORGANISM: Homo sapiens

<400> SEQUENCE: 18

```
Gln Tyr Glu Leu Thr Gln Pro Pro Ser Val Ser Val Tyr Pro Gly Gln
 1               5                  10                  15

Thr Ala Ser Ile Thr Cys Ser Gly Asp Gln Leu Gly Ser Lys Phe Val
                20                  25                  30

Ser Trp Tyr Gln Gln Arg Pro Gly Gln Ser Pro Val Leu Val Met Tyr
            35                  40                  45

Lys Asp Lys Arg Arg Pro Ser Glu Ile Pro Glu Arg Phe Ser Gly Ser
 50                  55                  60

Asn Ser Gly Asn Thr Ala Thr Leu Thr Ile Ser Gly Thr Gln Ala Ile
 65                  70                  75                  80

Asp Glu Ala Asp Tyr Tyr Cys Gln Ala Trp Asp Ser Ser Thr Tyr Val
                 85                  90                  95

Phe Gly Thr Gly Thr Lys Val Thr Val Leu
            100                 105
```

<210> SEQ ID NO 19
<211> LENGTH: 5
<212> TYPE: PRT
<213> ORGANISM: Homo sapiens

<400> SEQUENCE: 19

```
Ala Tyr Gly Met Gly
 1               5
```

<210> SEQ ID NO 20
<211> LENGTH: 17
<212> TYPE: PRT
<213> ORGANISM: Homo sapiens

<400> SEQUENCE: 20

```
Tyr Ile Ser Pro Ser Gly Gly His Thr Lys Tyr Ala Asp Ser Val Lys
 1               5                  10                  15

Gly
```

<210> SEQ ID NO 21
<211> LENGTH: 13
<212> TYPE: PRT
<213> ORGANISM: Homo sapiens

<400> SEQUENCE: 21

```
Val Leu Glu Thr Gly Leu Leu Val Asp Ala Phe Asp Ile
 1               5                  10
```

```
<210> SEQ ID NO 22
<211> LENGTH: 11
<212> TYPE: PRT
<213> ORGANISM: Homo sapiens

<400> SEQUENCE: 22

Ser Gly Asp Gln Leu Gly Ser Lys Phe Val Ser
1               5                   10

<210> SEQ ID NO 23
<211> LENGTH: 8
<212> TYPE: PRT
<213> ORGANISM: Homo sapiens

<400> SEQUENCE: 23

Tyr Lys Asp Lys Arg Arg Pro Ser
1               5

<210> SEQ ID NO 24
<211> LENGTH: 9
<212> TYPE: PRT
<213> ORGANISM: Homo sapiens

<400> SEQUENCE: 24

Gln Ala Trp Asp Ser Ser Thr Tyr Val
1               5

<210> SEQ ID NO 25
<211> LENGTH: 118
<212> TYPE: PRT
<213> ORGANISM: Homo sapiens

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Gly Met Gly Trp Val Arg Gln Ala Pro Gly Lys Gly Leu Glu Trp Val
        35                  40                  45

Ser Tyr Ile Ser Pro Ser Gly Gly Ile Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Asn Tyr Tyr Tyr Gly Leu Asp Val Trp Gly Gln Gly Thr
            100                 105                 110

Thr Val Thr Val Ser Ser
        115

<210> SEQ ID NO 26
<211> LENGTH: 108
<212> TYPE: PRT
<213> ORGANISM: Homo sapiens

<400> SEQUENCE: 26

Gln Asp Ile Gln Met Thr Gln Ser Pro Ser Ser Leu Ser Ala Ser Val
1               5                   10                  15

Gly Asp Arg Ile Thr Ile Thr Cys Gln Ala Ser Gln Asp Ile Gly Asp
            20                  25                  30
```

```
Ser Leu Asn Trp Tyr Gln Gln Lys Pro Gly Lys Ala Pro Arg Leu Leu
         35                  40                  45

Ile Tyr Asp Ala Ser Asn Leu Glu Thr Gly Val Pro Pro Arg Phe Ser
 50                  55                  60

Gly Ser Gly Ser Gly Thr Asp Phe Thr Phe Thr Phe Arg Ser Leu Gln
 65                  70                  75                  80

Pro Glu Asp Ile Ala Thr Tyr Phe Cys Gln Gln Ser Ala Asn Ala Pro
                 85                  90                  95

Phe Thr Phe Gly Pro Gly Thr Lys Val Asp Ile Lys
            100                 105

<210> SEQ ID NO 27
<211> LENGTH: 5
<212> TYPE: PRT
<213> ORGANISM: Homo sapiens

<400> SEQUENCE: 27

Trp Tyr Gly Met Gly
 1               5

<210> SEQ ID NO 28
<211> LENGTH: 17
<212> TYPE: PRT
<213> ORGANISM: Homo sapiens

<400> SEQUENCE: 28

Tyr Ile Ser Pro Ser Gly Gly Ile Thr Val Tyr Ala Asp Ser Val Lys
 1               5                  10                  15

Gly

<210> SEQ ID NO 29
<211> LENGTH: 9
<212> TYPE: PRT
<213> ORGANISM: Homo sapiens

<400> SEQUENCE: 29

Leu Asn Tyr Tyr Tyr Gly Leu Asp Val
 1               5

<210> SEQ ID NO 30
<211> LENGTH: 11
<212> TYPE: PRT
<213> ORGANISM: Homo sapiens

<400> SEQUENCE: 30

Gln Ala Ser Gln Asp Ile Gly Asp Ser Leu Asn
 1               5                  10

<210> SEQ ID NO 31
<211> LENGTH: 7
<212> TYPE: PRT
<213> ORGANISM: Homo sapiens

<400> SEQUENCE: 31

Asp Ala Ser Asn Leu Glu Thr
 1               5

<210> SEQ ID NO 32
<211> LENGTH: 9
<212> TYPE: PRT
<213> ORGANISM: Homo sapiens
```

```
<400> SEQUENCE: 32

Gln Gln Ser Ala Asn Ala Pro Phe Thr
1               5

<210> SEQ ID NO 33
<211> LENGTH: 119
<212> TYPE: PRT
<213> ORGANISM: Homo sapiens

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Trp Trp Val Arg Gln Ala Pro Gly Lys Gly Leu Glu Trp Val
        35                  40                  45

Ser Tyr Ile Gly Ser Ser Gly Pro Thr Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Arg Gly Thr Pro Tyr Tyr Phe Asp Ser Trp Gly Gln Gly
            100                 105                 110

Thr Leu Val Thr Val Ser Ser
        115

<210> SEQ ID NO 34
<211> LENGTH: 110
<212> TYPE: PRT
<213> ORGANISM: Homo sapiens

<400> SEQUENCE: 34

Gln Tyr Glu Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Arg Trp
            20                  25                  30

Asn Ile Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Trp Val Phe Gly Gly Gly Thr Lys Leu Thr Val Leu
            100                 105                 110

<210> SEQ ID NO 35
<211> LENGTH: 5
<212> TYPE: PRT
<213> ORGANISM: Homo sapiens

<400> SEQUENCE: 35

Arg Tyr Gly Met Trp
1               5
```

```
<210> SEQ ID NO 36
<211> LENGTH: 17
<212> TYPE: PRT
<213> ORGANISM: Homo sapiens

<400> SEQUENCE: 36

Tyr Ile Gly Ser Ser Gly Gly Pro Thr Tyr Tyr Val Asp Ser Val Lys
1               5                   10                  15
Gly

<210> SEQ ID NO 37
<211> LENGTH: 10
<212> TYPE: PRT
<213> ORGANISM: Homo sapiens

<400> SEQUENCE: 37

Gly Arg Gly Thr Pro Tyr Tyr Phe Asp Ser
1               5                   10

<210> SEQ ID NO 38
<211> LENGTH: 14
<212> TYPE: PRT
<213> ORGANISM: Homo sapiens

<400> SEQUENCE: 38

Thr Gly Thr Ser Ser Asp Ile Gly Arg Trp Asn Ile Val Ser
1               5                   10

<210> SEQ ID NO 39
<211> LENGTH: 7
<212> TYPE: PRT
<213> ORGANISM: Homo sapiens

<400> SEQUENCE: 39

Asp Val Ser Asn Arg Pro Ser
1               5

<210> SEQ ID NO 40
<211> LENGTH: 10
<212> TYPE: PRT
<213> ORGANISM: Homo sapiens

<400> SEQUENCE: 40

Ser Ser Tyr Thr Ser Ser Ser Thr Trp Val
1               5                   10

<210> SEQ ID NO 41
<211> LENGTH: 1323
<212> TYPE: PRT
<213> ORGANISM: Homo sapiens

<400> SEQUENCE: 41

Ser Glu Val Gly Asn Ser Gln Ala Val Cys Pro Gly Thr Leu Asn Gly
1               5                   10                  15

Leu Ser Val Thr Gly Asp Ala Glu Asn Gln Tyr Gln Thr Leu Tyr Lys
                20                  25                  30

Leu Tyr Glu Arg Cys Glu Val Val Met Gly Asn Leu Glu Ile Val Leu
            35                  40                  45

Thr Gly His Asn Ala Asp Leu Ser Phe Leu Gln Trp Ile Arg Glu Val
        50                  55                  60

Thr Gly Tyr Val Leu Val Ala Met Asn Glu Phe Ser Thr Leu Pro Leu
65                  70                  75                  80
```

-continued

```
Pro Asn Leu Arg Val Arg Gly Thr Gln Val Tyr Asp Gly Lys Phe
             85                  90                  95

Ala Ile Phe Val Met Leu Asn Tyr Asn Thr Asn Ser Ser His Ala Leu
            100                 105                 110

Arg Gln Leu Arg Leu Thr Gln Leu Thr Glu Ile Leu Ser Gly Gly Val
            115                 120                 125

Tyr Ile Glu Lys Asn Asp Lys Leu Cys His Met Asp Thr Ile Asp Trp
        130                 135                 140

Arg Asp Ile Val Arg Asp Arg Asp Ala Glu Ile Val Val Lys Asp Asn
145                 150                 155                 160

Gly Arg Ser Cys Pro Pro Cys His Glu Val Cys Lys Gly Arg Cys Trp
                165                 170                 175

Gly Pro Gly Ser Glu Asp Cys Gln Thr Leu Thr Lys Thr Ile Cys Ala
            180                 185                 190

Pro Gln Cys Asn Gly His Cys Phe Gly Pro Asn Pro Asn Gln Cys Cys
        195                 200                 205

His Asp Glu Cys Ala Gly Gly Cys Ser Gly Pro Gln Asp Thr Asp Cys
    210                 215                 220

Phe Ala Cys Arg His Phe Asn Asp Ser Gly Ala Cys Val Pro Arg Cys
225                 230                 235                 240

Pro Gln Pro Leu Val Tyr Asn Lys Leu Thr Phe Gln Leu Glu Pro Asn
                245                 250                 255

Pro His Thr Lys Tyr Gln Tyr Gly Gly Val Cys Val Ala Ser Cys Pro
            260                 265                 270

His Asn Phe Val Val Asp Gln Thr Ser Cys Val Arg Ala Cys Pro Pro
        275                 280                 285

Asp Lys Met Glu Val Asp Lys Asn Gly Leu Lys Met Cys Glu Pro Cys
    290                 295                 300

Gly Gly Leu Cys Pro Lys Ala Cys Glu Gly Thr Gly Ser Gly Ser Arg
305                 310                 315                 320

Phe Gln Thr Val Asp Ser Ser Asn Ile Asp Gly Phe Val Asn Cys Thr
                325                 330                 335

Lys Ile Leu Gly Asn Leu Asp Phe Leu Ile Thr Gly Leu Asn Gly Asp
            340                 345                 350

Pro Trp His Lys Ile Pro Ala Leu Asp Pro Glu Lys Leu Asn Val Phe
        355                 360                 365

Arg Thr Val Arg Glu Ile Thr Gly Tyr Leu Asn Ile Gln Ser Trp Pro
    370                 375                 380

Pro His Met His Asn Phe Ser Val Phe Ser Asn Leu Thr Thr Ile Gly
385                 390                 395                 400

Gly Arg Ser Leu Tyr Asn Arg Gly Phe Ser Leu Leu Ile Met Lys Asn
                405                 410                 415

Leu Asn Val Thr Ser Leu Gly Phe Arg Ser Leu Lys Glu Ile Ser Ala
            420                 425                 430

Gly Arg Ile Tyr Ile Ser Ala Asn Arg Gln Leu Cys Tyr His His Ser
        435                 440                 445

Leu Asn Trp Thr Lys Val Leu Arg Gly Pro Thr Glu Glu Arg Leu Asp
    450                 455                 460

Ile Lys His Asn Arg Pro Arg Arg Asp Cys Val Ala Glu Gly Lys Val
465                 470                 475                 480

Cys Asp Pro Leu Cys Ser Ser Gly Gly Cys Trp Gly Pro Gly Pro Gly
                485                 490                 495
```

-continued

```
Gln Cys Leu Ser Cys Arg Asn Tyr Ser Arg Gly Val Cys Val Thr
            500                 505                 510
His Cys Asn Phe Leu Asn Gly Glu Pro Arg Glu Phe Ala His Glu Ala
        515                 520                 525
Glu Cys Phe Ser Cys His Pro Glu Cys Gln Pro Met Glu Gly Thr Ala
        530                 535                 540
Thr Cys Asn Gly Ser Gly Ser Asp Thr Cys Ala Gln Cys Ala His Phe
545                 550                 555                 560
Arg Asp Gly Pro His Cys Val Ser Ser Cys Pro His Gly Val Leu Gly
                565                 570                 575
Ala Lys Gly Pro Ile Tyr Lys Tyr Pro Asp Val Gln Asn Glu Cys Arg
            580                 585                 590
Pro Cys His Glu Asn Cys Thr Gln Gly Cys Lys Gly Pro Glu Leu Gln
            595                 600                 605
Asp Cys Leu Gly Gln Thr Leu Val Leu Ile Gly Lys Thr His Leu Thr
            610                 615                 620
Met Ala Leu Thr Val Ile Ala Gly Leu Val Val Ile Phe Met Met Leu
625                 630                 635                 640
Gly Gly Thr Phe Leu Tyr Trp Arg Gly Arg Arg Ile Gln Asn Lys Arg
                645                 650                 655
Ala Met Arg Arg Tyr Leu Glu Arg Gly Glu Ser Ile Glu Pro Leu Asp
            660                 665                 670
Pro Ser Glu Lys Ala Asn Lys Val Leu Ala Arg Ile Phe Lys Glu Thr
            675                 680                 685
Glu Leu Arg Lys Leu Lys Val Leu Gly Ser Gly Val Phe Gly Thr Val
        690                 695                 700
His Lys Gly Val Trp Ile Pro Glu Gly Glu Ser Ile Lys Ile Pro Val
705                 710                 715                 720
Cys Ile Lys Val Ile Glu Asp Lys Ser Gly Arg Gln Ser Phe Gln Ala
                725                 730                 735
Val Thr Asp His Met Leu Ala Ile Gly Ser Leu Asp His Ala His Ile
            740                 745                 750
Val Arg Leu Leu Gly Leu Cys Pro Gly Ser Ser Leu Gln Leu Val Thr
        755                 760                 765
Gln Tyr Leu Pro Leu Gly Ser Leu Leu Asp His Val Arg Gln His Arg
770                 775                 780
Gly Ala Leu Gly Pro Gln Leu Leu Leu Asn Trp Gly Val Gln Ile Ala
785                 790                 795                 800
Lys Gly Met Tyr Tyr Leu Glu Glu His Gly Met Val His Arg Asn Leu
                805                 810                 815
Ala Ala Arg Asn Val Leu Leu Lys Ser Pro Ser Gln Val Gln Val Ala
            820                 825                 830
Asp Phe Gly Val Ala Asp Leu Leu Pro Pro Asp Asp Lys Gln Leu Leu
            835                 840                 845
Tyr Ser Glu Ala Lys Thr Pro Ile Lys Trp Met Ala Leu Glu Ser Ile
        850                 855                 860
His Phe Gly Lys Tyr Thr His Gln Ser Asp Val Trp Ser Tyr Gly Val
865                 870                 875                 880
Thr Val Trp Glu Leu Met Thr Phe Gly Ala Glu Pro Tyr Ala Gly Leu
                885                 890                 895
Arg Leu Ala Glu Val Pro Asp Leu Leu Glu Lys Gly Glu Arg Leu Ala
            900                 905                 910
```

-continued

Gln Pro Gln Ile Cys Thr Ile Asp Val Tyr Met Val Met Val Lys Cys
            915                 920                 925

Trp Met Ile Asp Glu Asn Ile Arg Pro Thr Phe Lys Glu Leu Ala Asn
    930                 935                 940

Glu Phe Thr Arg Met Ala Arg Asp Pro Pro Arg Tyr Leu Val Ile Lys
945                 950                 955                 960

Arg Glu Ser Gly Pro Gly Ile Ala Pro Gly Pro Glu Pro His Gly Leu
                965                 970                 975

Thr Asn Lys Lys Leu Glu Val Glu Leu Pro Glu Leu Asp Leu
            980                 985                 990

Asp Leu Asp Leu Glu Ala Glu Glu Asp Asn Leu Ala Thr Thr Thr Leu
            995                 1000                1005

Gly Ser Ala Leu Ser Leu Pro Val Gly Thr Leu Asn Arg Pro Arg
    1010            1015                1020

Gly Ser Gln Ser Leu Leu Ser Pro Ser Ser Gly Tyr Met Pro Met
    1025            1030                1035

Asn Gln Gly Asn Leu Gly Glu Ser Cys Gln Glu Ser Ala Val Ser
    1040            1045                1050

Gly Ser Ser Glu Arg Cys Pro Arg Pro Val Ser Leu His Pro Met
    1055            1060                1065

Pro Arg Gly Cys Leu Ala Ser Glu Ser Ser Glu Gly His Val Thr
    1070            1075                1080

Gly Ser Glu Ala Glu Leu Gln Glu Lys Val Ser Met Cys Arg Ser
    1085            1090                1095

Arg Ser Arg Ser Arg Ser Pro Arg Pro Arg Gly Asp Ser Ala Tyr
    1100            1105                1110

His Ser Gln Arg His Ser Leu Leu Thr Pro Val Thr Pro Leu Ser
    1115            1120                1125

Pro Pro Gly Leu Glu Glu Glu Asp Val Asn Gly Tyr Val Met Pro
    1130            1135                1140

Asp Thr His Leu Lys Gly Thr Pro Ser Ser Arg Glu Gly Thr Leu
    1145            1150                1155

Ser Ser Val Gly Leu Ser Ser Val Leu Gly Thr Glu Glu Glu Asp
    1160            1165                1170

Glu Asp Glu Glu Tyr Glu Tyr Met Asn Arg Arg Arg Arg His Ser
    1175            1180                1185

Pro Pro His Pro Pro Arg Pro Ser Ser Leu Glu Glu Leu Gly Tyr
    1190            1195                1200

Glu Tyr Met Asp Val Gly Ser Asp Leu Ser Ala Ser Leu Gly Ser
    1205            1210                1215

Thr Gln Ser Cys Pro Leu His Pro Val Pro Ile Met Pro Thr Ala
    1220            1225                1230

Gly Thr Thr Pro Asp Glu Asp Tyr Glu Tyr Met Asn Arg Gln Arg
    1235            1240                1245

Asp Gly Gly Gly Pro Gly Gly Asp Tyr Ala Ala Met Gly Ala Cys
    1250            1255                1260

Pro Ala Ser Glu Gln Gly Tyr Glu Glu Met Arg Ala Phe Gln Gly
    1265            1270                1275

Pro Gly His Gln Ala Pro His Val His Tyr Ala Arg Leu Lys Thr
    1280            1285                1290

Leu Arg Ser Leu Glu Ala Thr Asp Ser Ala Phe Asp Asn Pro Asp
    1295            1300                1305

```
Tyr Trp  His Ser Arg Leu Phe  Pro Lys Ala Asn Ala  Gln Arg Thr
    1310             1315             1320
```

USE OF ERBB3 INHIBITORS IN THE TREATMENT OF TRIPLE NEGATIVE AND BASAL-LIKE BREAST CANCERS

CROSS-REFERENCE TO RELATED APPLICATION

This application is a continuation of U.S. application Ser. No. 13/583,949, filed Sep. 11, 2012, which is a 35 U.S.C. 371 national stage filing of International Application No. PCT/US2011/028129, filed Mar. 11, 2011, which claims priority to U.S. Provisional Patent Application No. 61/312,895, filed Mar. 11, 2010. The entire contents of the aforementioned and any patents, patent applications, or references cited throughout this specification are hereby incorporated by reference in their entireties.

BACKGROUND

In women, breast cancer is among the most common cancers and is the fifth most common cause of cancer deaths. Due to the heterogeneity of breast cancers, 10-year progression free survival can vary widely with stage and type, from 98% to 10%. Different forms of breast cancers can have remarkably different biological characteristics and clinical behavior. Thus, classification of a patient's breast cancer has become a critical component for determining a treatment regimen. For example, along with classification of histological type and grade, breast cancers now are routinely evaluated for expression of hormone receptors (estrogen receptor (ER) and progesterone receptor (PR)) and for expression of HER2 (ErbB2), since a number of treatment modalities are currently available that target hormone receptors or the HER2 receptor. ER and PR are both nuclear receptors (they are predominantly located at cell nuclei, although they can also be found at the cell membrane) and small molecular inhibitors that target ER and/or PR have been developed. HER2, or human epidermal growth factor receptor type 2, is a receptor normally located on the cell surface and antibodies that target HER2 have been developed as therapeutics. HER2 is the only member of the EGFR family (which also includes HER1 (EGFR), HER3 (ErbB3) and HER4 (ErbB4) that is not capable of binding to an activating ligand on its own. Thus HER2 is only functional as a receptor when incorporated into a heterodimeric receptor complex with another EGFR family member, such as HER3. Cancers classified as expressing the estrogen receptor (estrogen receptor positive, or ER$^+$ tumors) may be treated with an ER antagonist such as tamoxifen. Similarly, breast cancers classified as expressing high levels the HER2 receptor may be treated with an anti-HER2 antibody, such as trastuzumab, or with a HER2-active receptor tyrosine kinase inhibitor such as lapatinib.

Triple negative (TN) breast cancer is a term used to designate a well-defined clinically relevant subtype of breast carcinomas that account for approximately 15% of all breast cancer cases. TN tumors score negative (i.e., using conventional histopathology methods and criteria) for expression of ER and PR and do not express amplified levels of HER2 (i.e., they are ER$^-$, PR$^-$, HER2$^-$). TN breast cancer comprises primarily, but not exclusively, a molecularly and histopathologically distinct subtype of breast cancer known as the basal-like (BL) subtype. The BL subtype also is characterized by the expression of cytokeratins (e.g., CK, CK5/6, CK14, CK17) and other proteins found in normal basal/myoepithelial cells of the breast. However, in addition to the BL subtype, certain other types of breast cancers, including some "normal breast-like", metaplastic carcinomas, medullary carcinomas and salivary gland-like tumors can also exhibit the triple negative (TN) phenotype. Furthermore, TN breast cancers occur more frequently in the presence of BRCA1 mutations and in pre-menopausal females of African-American or Hispanic descent. TN tumors typically display very aggressive behavior, with shorter post-relapse survival and poor overall survival rates relative to other breast cancer types.

Not all BL breast cancers are TN. Basal-like breast tumors are a heterogeneous tumor type that account for up to 15% of all breast cancers and exhibit aggressive clinical behavior that makes them particularly difficult to treat successfully. A majority of BL breast cancers are ER-, PR-, and HER2 low (HER2$^{1+}$ or HER2 negative). In addition, they typically express proteins usually found in normal breast basal (myoepithelial) cells. These include high molecular weight cytokeratins (e.g., 5/6, 8, 14, 17 and 18), p-cadherin, caveolins 1 and 2, nestin, aB crystalline, and EGFR. Furthermore, BL tumor cells typically lack the capacity for competent homologous recombination DNA repair.

Histologically, most BL breast cancers are of IDC-NST type, high histological grade, and exhibit very high mitotic indices. They also typically have central necrotic or fibrotic zones, pushing borders, conspicuous lymphocytic infiltrates, and typical/atypical medullary features, and generally exhibit features similar to those of human papilloma virus-induced squamous cell carcinoma of the head and neck.

A great majority of medullary and atypical medullary, metaplastic, secretory, myoepithelial, and adenoid cystic carcinomas of the breast also exhibit BL characteristics.

Given the lack of expression of hormone receptors or of significant amounts of HER2 in TN breast cancer cells, treatment options have been very limited as the tumors are not responsive to treatments that target ER (e.g., tamoxifen, aromatase inhibitors) or HER2 (e.g., trastuzumab). Instead these tumors are treated with conventional neoadjuvant and adjuvant chemotherapy regimens, which have limited efficacy and many cytotoxic side effects. Furthermore, such chemotherapy regimens can lead to drug resistance in tumors, and the risk of recurrence of disease in TN breast cancers is higher within the first three years of treatment than for other types of breast cancers.

Basal-like breast cancers are also difficult to treat and are associated with poor prognoses, though BL adenoid cystic carcinomas generally are associated with better clinical outcomes.

In view of the foregoing, a need remains for additional treatment options and methods for treating triple negative breast cancers and BL breast cancers.

SUMMARY

Provided herein are methods for treating triple negative breast cancers (e.g., tumors) and basal-like breast cancers (e.g., tumors), as well as pharmaceutical compositions that can be used in such methods. The methods and compositions are based, at least in part, on the discovery that ErbB3 inhibition can suppress the growth of TN breast cancer cells and BL breast cancer cells. In particular, administration of anti-ErbB3 antibody is demonstrated to suppress the growth of TN breast cancer cells in vivo.

Accordingly, use of an ErbB3 inhibitor (e.g., use thereof for the manufacture of a medicament) for the treatment of TN or BL breast cancer is provided. In another aspect, a method of suppressing growth of a TN breast cancer tumor or a BL breast cancer tumor is provided, the method comprising contacting the tumor with an effective amount of an ErbB3 inhibitor. In another aspect, a method of suppressing growth of a TN breast cancer tumor or BL breast cancer tumor in a patient is provided, the method comprising administering to the patient an effective amount of an ErbB3 inhibitor. In yet another aspect, a method of treating a patient for a TN breast cancer tumor or BL breast cancer tumor is provided, the method comprising administering to the patient an effective amount of an ErbB3 inhibitor. In still another aspect, a method of treating a breast cancer tumor or BL breast cancer tumor in a patient is provided, the method comprising: selecting a patient with a triple negative breast cancer tumor or a BL breast cancer tumor; and administering to the patient an effective amount of an ErbB3 inhibitor.

In an exemplary embodiment, the ErbB3 inhibitor is an anti-ErbB3 antibody. An exemplary anti-ErbB3 antibody is MM-121 (Ab #6), comprising $V_H$ and $V_L$ sequences as shown in SEQ ID NOs: 1 and 2, respectively. Another exemplary anti-ErbB3 antibody is an antibody comprising, optionally in amino terminal to carboxy terminal order, $V_H$ CDR1, 2 and 3 sequences as shown in SEQ ID NOs: 3-5, respectively, and, optionally in amino terminal to carboxy terminal order, $V_L$ CDR1, 2 and 3 sequences as shown in SEQ ID NOs: 6-8, respectively. In other embodiments, the anti-ErbB3 antibody is Ab #3 (comprising $V_H$ and $V_L$ sequences as shown in SEQ ID NOs: 9 and 10, respectively), Ab #14 (comprising $V_H$ and $V_L$ sequences as shown in SEQ ID NOs: 17 and 18, respectively), Ab #17 (comprising $V_H$ and $V_L$ sequences as shown in SEQ ID NOs: 25 and 26, respectively) or Ab #19 (comprising $V_H$ and $V_L$ sequences as shown in SEQ ID NOs: 33 and 34, respectively). In still other embodiments, the anti-ErbB3 antibody is selected from the group consisting of mAb 1B4C3, mAb 2D1D12, AMG-888 and humanized mAb 8B8. In another embodiment, administration of the anti-ErbB3 antibody inhibits growth or invasiveness or metastasis of the tumor.

The methods provided herein can be used in the treatment of TN breast cancers of various different histopathological phenotypes. For example, in one embodiment, the triple negative breast cancer tumor is histopathologically characterized as having a basal-like phenotype. In another embodiment, the TN breast cancer tumor is histopathologically characterized as having a phenotype other than BL.

In each of the foregoing methods and compositions, the ErbB3 inhibitor may be comprised in a formulation comprising a pharmaceutically acceptable carrier.

In another aspect, the treatment methods provided herein further comprise administering to the patient at least one additional anti-cancer agent that is not an ErbB3 inhibitor. In one embodiment, the at least one additional anti-cancer agent comprises at least one chemotherapeutic drug, such as a drug(s) selected from the group consisting of platinum-based chemotherapy drugs, taxanes, tyrosine kinase inhibitors, and combinations thereof. It has now been observed that in the subset of TN breast cancers that test HER2$^{2\pm}$, treatment with anti-HER2 agents such as trastuzumab, pertuzumab or lapatinib may provide benefits when used in combination with anti-ErbB3 antibodies. Thus in another aspect the treatment methods provided herein further comprise administering to the patient an effective amount of at least one additional anti-cancer agent that is an anti-HER2 agent. Such anti-HER2 agents are well known and may include one or more of anti-ErbB2 antibodies such as C6.5 (and the numerous derivatives thereof) described in U.S. Pat. No. 5,977,322, trastuzumab, as described in U.S. Pat. No. 6,054,297, and pertuzumab, as described in U.S. Pat. No. 6,949,245; as well as small molecule anti-HER2 agents such as lapatinib (which also inhibits EGFR tyrosine kinase) and AG879.

In another embodiment, the at least one additional anti-cancer agent comprises an EGFR inhibitor, such as an anti-EGFR antibody or a small molecule inhibitor of EGFR signaling. An exemplary anti-EGFR antibody comprises cetuximab. Other examples of anti-EGFR antibodies include matuzumab, panitumumab, nimotuzumab and mAb 806. An exemplary small molecule inhibitor of EGFR signaling comprises gefitinib. Other examples of useful small molecule inhibitors of EGFR signaling include lapatinib, canertinib, erlotinib HCL, pelitinib, PKI-166, PD158780, and AG 1478.

In yet another embodiment, the at least one additional anti-cancer agent comprises a VEGF inhibitor. An exemplary VEGF inhibitor comprises an anti-VEGF antibody, such as the bevacizumab antibody.

In another embodiment, administration of the anti-ErbB3 antibody and the at least one additional anti-cancer agent inhibits growth or invasiveness or metastasis of the tumor.

In another aspect, methods of treating TN breast cancer or BL breast cancer in a patient comprise administering to said patient a combination comprising MM-121 and paclitaxel. In one embodiment the combination exhibits therapeutic synergy in the treatment of TN or BL breast cancers. In some examples, the combination effects a $\log_{in}$ cell kill of at least 2.8, at least 2.9 or at least 3.0. In other aspects, the combination provides an improvement in tumor growth inhibition that is at least about additive as compared to improvement obtained with each of the single agents of the combination.

In another embodiment, there is provided a composition comprising a combination of MM-121 and paclitaxel, wherein the combination exhibits therapeutic synergy in the treatment of TN or BL breast cancers. In some examples, the composition effects a $\log_{10}$ cell kill of at least 2.8, at least 2.9 or at least 3.0.

Kits containing the combination pharmaceutical compositions also are provided.

BRIEF DESCRIPTION OF THE DRAWINGS

FIG. 4A depicts treatment with MM-121, cetuximab, or paclitaxel; MM-121 and cetuximab; and the triple combination MM-121 and cetuximab and paclitaxel. FIG. 4B depicts treatment with MM-121, erlotinib, MM-121 and erlotinib, or the triple combination of MM-121 and erlotinib and paclitaxel.

DETAILED DESCRIPTION

Figure 1:
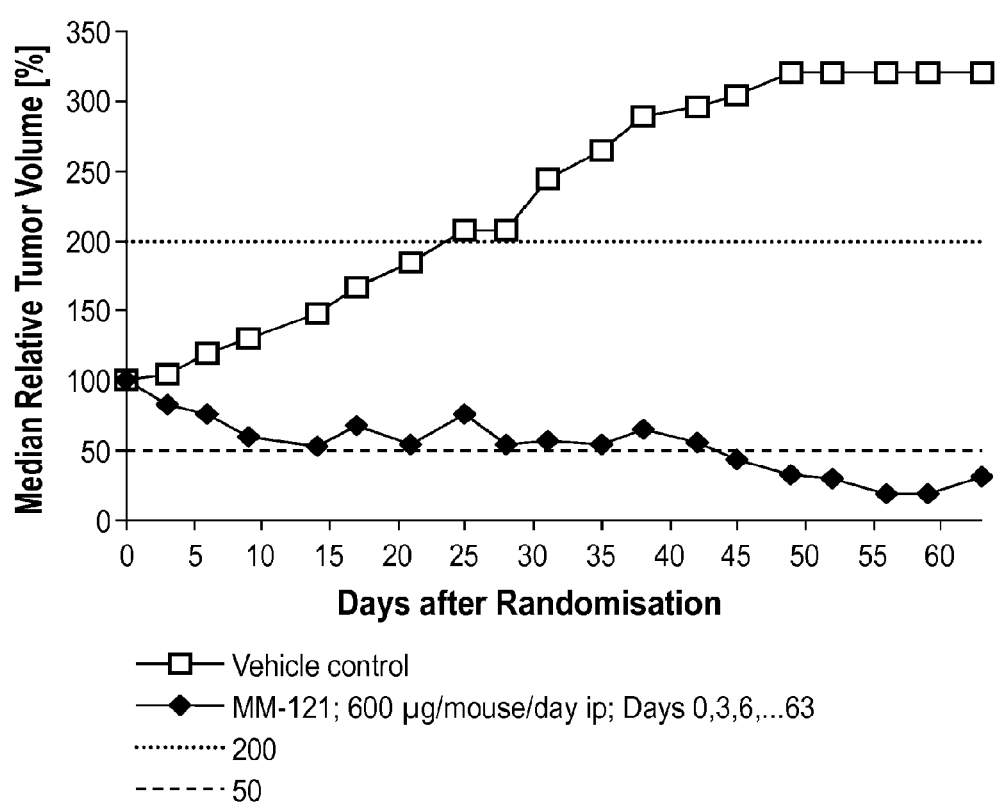
FIG. 1 is a graph showing relative MAXF449 xenograft tumor volume (%) (Y axis—normalized to initial tumor volume) plotted against time in days following randomization (X axis) in NMRI nude mice treated with MM-121 or vehicle control. TGI=200%.

Provided herein are methods for treating triple negative and basal-like breast cancers, as well as pharmaceutical compositions that can be used in practicing such methods. As described further in the Examples, it has now been demonstrated that an ErbB3 inhibitor, in particular an anti-ErbB3 antibody, is able to suppress the growth of TN breast cancer cells in vivo. Accordingly, methods for suppressing the growth of TN breast cancers and BL breast cancers, as well as methods of treating such breast cancers in patients, using an ErbB3 inhibitor are provided herein.

Definitions:

As used herein, the term "triple negative" or "TN" refers to tumors (e.g., carcinomas), typically breast tumors, in which the tumor cells score negative (i.e., using conventional histopathology methods) for estrogen receptor (ER) and progesterone receptor (PR), both of which are nuclear receptors (i.e., they are predominantly located at cell nuclei), and the tumor cells are not amplified for epidermal growth factor receptor type 2 (HER2 or ErbB2), a receptor normally located on the cell surface. Tumor cells are considered negative for expression of ER and PR if less than 5% of the tumor cell nuclei are stained for ER and PR expression using standard immunohistochemical techniques. Tumor cells are considered highly amplified for HER2 ("HER2$^{3+}$") if, when tested with a HercepTest™ Kit (Code K5204, Dako North America, Inc., Carpinteria, Calif.), a semi-quantitative immunohistochemical assay using a polyclonal anti-HER2 primary antibody, they yield a test result score of 3+, or, the test HER2 positive by fluorescence in-situ hybridization (FISH). As used herein, tumor cells are considered negative for HER2 overexpression if they yield a test result score of 0 or 1+, or 2+, or if they are HER2 FISH negative.

Furthermore, the term "triple negative breast cancer(s)" or "TN breast cancer(s)" encompasses carcinomas of differing histopathological phenotypes. For example, certain TN breast cancers are classified as "basal-like" ("BL"), in which the neoplastic cells express genes usually found in normal basal/myoepithelial cells of the breast, such as high molecular weight basal cytokeratins (CK, CK5/6, CK14, CK17), vimentin, p-cadherin, αB crystallin, fascin and caveolins 1 and 2. Certain other TN breast cancers, however, have a different histopathological phenotype, examples of which include high grade invasive ductal carcinoma of no special type, metaplastic carcinomas, medullary carcinomas and salivary gland-like tumors of the breast.

The terms "ErbB3," "HER3," "ErbB3 receptor," and "HER3 receptor," as used interchangeably herein, refer to human ErbB3 protein, as described in U.S. Pat. No. 5,480,968.

As used herein, the term "ErbB3 inhibitor" is intended to include therapeutic agents that inhibit, downmodulate, suppress or downregulate activity of ErbB3. The term is intended to include chemical compounds, such as small molecule inhibitors, and biologic agents, such as antibodies, interfering RNA (shRNA, siRNA), soluble receptors and the like. An exemplary ErbB3 inhibitor is an anti-ErbB3 antibody.

An "antibody," as used herein is a protein consisting of one or more polypeptides comprising binding domains substantially encoded by immunoglobulin genes or fragments of immunoglobulin genes, wherein the protein immunospecifically binds to an antigen. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin structural unit comprises a tetramer that is composed of two identical pairs of polypeptide chains, each pair having one "light" (about 25 kD) and one "heavy" chain (about 50-70 kD). "$V_L$" and $V_H$" refer to these light and heavy chains respectively.

Antibodies include intact immunoglobulins as well as antigen-binding fragments thereof, which may be produced by digestion with various peptidases, or synthesized de novo either chemically or using recombinant DNA expression technology. Such fragments include, for example, $F(ab)_2$ dimers and Fab monomers. Useful antibodies include single chain antibodies (antibodies that exist as a single polypeptide chain), e.g., single chain Fv antibodies (scFv) in which a $V_H$ and a $V_L$ chain are joined together (directly or through a peptide linker) to form a continuous polypeptide.

"Immunospecific" or "immunospecifically" refer to antibodies that bind via domains substantially encoded by immunoglobulin genes or fragments of immunoglobulin genes to one or more epitopes of a protein of interest, but which do not substantially recognize and bind other molecules in a sample containing a mixed population of antigenic molecules. Typically, an antibody binds immunospecifically to a cognate antigen with a $K_d$ with a value of no greater than 50 nM, as measured by a surface plasmon resonance assay or a cell binding assay. The use of such assays is well known in the art, and is described in Example 3, below.

An "anti-ErbB3 antibody" is an antibody that immunospecifically binds to the ectodomain of ErbB3 and an "anti-ErbB2 antibody" is an antibody that immunospecifically binds to the ectodomain of ErbB2. The antibody may be an isolated antibody. Such binding to ErbB3 or ErB2 exhibits a $K_d$ with a value of no greater than 50 nM as measured by a surface plasmon resonance assay or a cell binding assay. An anti-ErbB3 antibody may be an isolated antibody. Exemplary anti-ErbB3 antibodies inhibit EGF-like ligand mediated phosphorylation of ErbB3. EGF-like ligands include EGF, TGFα, betacellulin, heparin-binding epidermal growth factor, biregulin, epigen, epiregulin, and amphiregulin, which typically bind to ErbB1 and induce heterodimerization of ErbB1 with ErbB3.

As used herein, the term "EGFR inhibitor" is intended to include therapeutic agents that inhibit, downmodulate, suppress or downregulate EGFR signaling activity. The term is intended to include chemical compounds, such as small molecule inhibitors (e.g., small molecule tyrosine kinase inhibitors) and biologic agents, such as antibodies, interfering RNA (shRNA, siRNA), soluble receptors and the like.

As used herein, the term "VEGF inhibitor" is intended to include therapeutic agents that inhibit, downmodulate, suppress or downregulate VEGF signaling activity. The term is intended to include chemical compounds, such as small molecule inhibitors (e.g., small molecule tyrosine kinase inhibitors) and biologic agents, such as antibodies, interfering RNA (shRNA, siRNA), soluble receptors and the like.

The terms "suppress", "suppression", "inhibit" and "inhibition" as used interchangeably herein, refer to any statistically significant decrease in biological activity (e.g., tumor cell growth), including full blocking of the activity. For example, "inhibition" can refer to a decrease of about 10%, 20%, 30%, 40%, 50%, 60%, 70%, 80%, 90%, or 100% in biological activity.

The term "patient" includes a human or other mammalian animal that receives either prophylactic or therapeutic treatment.

The terms "treat," "treating," and "treatment," as used herein, refer to therapeutic or preventative measures such as those described herein. The methods of "treatment" employ administration to a patient of an ErbB3 inhibitor provided herein, for example, a patient having a TN or BL breast cancer tumor, in order to prevent, cure, delay, reduce the severity of, or ameliorate one or more symptoms of the disease or disorder or recurring disease or disorder, or in order to prolong the survival of a patient beyond that expected in the absence of such treatment.

The term "effective amount," as used herein, refers to that amount of an agent, such as an ErbB3 inhibitor, for example an anti-ErbB3 antibody, which is sufficient to effect treatment, prognosis or diagnosis of a TN or BL breast cancer, when administered to a patient. A therapeutically effective amount will vary depending upon the patient and disease condition being treated, the weight and age of the patient, the severity of the disease condition, the manner of administration and the like, which can readily be determined by one of ordinary skill in the art. The dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of an antibody or antigen binding portion thereof, as provided herein. Dosing may be, e.g., every week, every 2 weeks, every three weeks, every 4 weeks, every 5 weeks or every 6 weeks. Dosage regimens may be adjusted to provide the optimum therapeutic response. An effective amount is also one in which any toxic or detrimental effects (side effects) of the agent are minimized and/or outweighed by the beneficial effects. For MM-121, administration may be intravenous at exactly or about 6 mg/kg or 12 mg/kg weekly, or 12 mg/kg or 24 mg/kg biweekly. Additional dosing regimens are described below.

The terms "anti-cancer agent" and "antineoplastic agent" refer to drugs used to treat malignancies, such as cancerous growths. Drug therapy may be used alone, or in combination with other treatments such as surgery or radiation therapy.

Various aspects and embodiments are described in further detail in the following subsections.

I. ErbB3 Inhibitors

As described in further detail herein, the methods and compositions provided herein involve the use of one or more ErbB3 inhibitors.

In one embodiment, the ErbB3 inhibitor is an anti-ErbB3 antibody, e.g., a monoclonal antibody. An exemplary anti-ErbB3 monoclonal antibody is MM-121, described further in WO 2008/100624 and U.S. Pat. No. 7,846,440, and having $V_H$ and $V_L$ sequences as shown in SEQ ID NOs: 1 and 2, respectively. Alternately, the anti-ErbB3 monoclonal antibody is an antibody that competes with MM-121 for binding to ErbB3. In another embodiment, the anti-ErbB3 antibody is an antibody comprising the $V_H$ and $V_L$ CDR sequences of MM-121, which are shown in SEQ ID NOs: 3-5 ($V_H$ CDR1, 2, 3) and 6-8 ($V_L$ CDR1, 2, 3), respectively. Other examples of anti-ErbB3 antibodies include Ab #3, Ab #14, Ab #17 and Ab #19, also described further in WO 2008/100624 and having $V_H$ and $V_L$ sequences as shown in SEQ ID NOs: 9 and 10, 17 and 18, 25 and 26, and 33 and 34 respectively. In another embodiment, the anti-ErbB3 antibody is an antibody comprising the $V_H$ and $V_L$ CDR sequences of Ab #3 (shown in SEQ ID NOs: 11-13 and 14-18, respectively) or antibody comprising the $V_H$ and $V_L$ CDR sequences of Ab #14 (shown in SEQ ID NOs: 19-21 and 22-24, respectively) or an antibody comprising the $V_H$ and $V_L$ CDR sequences of Ab #17 (shown in SEQ ID NOs: 27-29 and 30-32, respectively) or an antibody comprising the $V_H$ and $V_L$ CDR sequences of Ab #19 (shown in SEQ ID NOs: 35-37 and 38-40, respectively).

Alternately, the anti-ErbB3 antibody is a monoclonal antibody or antigen binding portion thereof which binds an epitope of human ErbB3 comprising residues 92-104 of SEQ ID NO:41 and is characterized by inhibition of proliferation of a cancer cell expressing ErbB3. The cancer cell may be a MALME-3M cell, an AdrR cell, or an ACHN cell and the proliferation may be reduced by at least 10% relative to control. In an additional embodiment this isolated monoclonal antibody or antigen binding portion thereof binds an epitope comprising residues 92-104 and 129 of SEQ ID NO:41.

Other examples of useful anti-ErbB3 antibodies include the antibodies 1B4C3 and 2D1D12 (U3 Pharma AG), both of which are described in US Patent Application Publication No. 20040197332 by Ullrich et al., and monoclonal antibodies (including humanized versions thereof), such as AMG-888 (U3 Pharma AG and Amgen) and 8B8, as described in U.S. Pat. No. 5,968,511 by Akita et al.

In yet another embodiment, the anti-ErbB3 antibody can comprise a mixture, or cocktail, of two or more anti-ErbB3 antibodies, each of which binds to a different epitope on ErbB3. In one embodiment, the mixture, or cocktail, comprises three anti-ErbB3 antibodies, each of which binds to a different epitope on ErbB3.

In another embodiment, the ErbB3 inhibitor comprises a nucleic acid molecule, such as an RNA molecule, that inhibits the expression or activity of ErbB3. RNA antagonists of ErbB3 have been described in the art (see e.g., US Patent Application Publication No. 20080318894). More-over, interfering RNAs specific for ErbB3, such as shRNAs or siRNAs that specifically inhibits the expression and/or activity of ErbB3, have been described in the art.

In yet another embodiment, the ErbB3 inhibitor comprises a soluble form of the ErbB3 receptor that inhibits signaling through the ErbB3 pathway. Such soluble ErbB3 molecules have been described in the art (see e.g., U.S. Pat. No. 7,390,632, U.S. Patent Application Publication No. 20080274504 and U.S. Patent Application Publication No. 20080261270, each by Maihle et al., and U.S. Patent Application Publication No. 20080057064 by Zhou).

II. Methods

In one aspect, use of an ErbB3 inhibitor for the manufacture of a medicament for the treatment of TN breast cancer or BL breast cancer is provided.

In another aspect, a method of suppressing growth of a triple negative breast cancer cell is provided, the method comprising contacting the cell with an effective amount of an ErbB3 inhibitor.

In another aspect, a method of suppressing growth of a TN or BL breast cancer tumor in a patient is provided, the method comprising administering to the patient an effective amount of an ErbB3 inhibitor.

In yet another aspect, a method of treating a patient for a TN or BL breast cancer tumor is provided, the method comprising administering to the patient an effective amount of an ErbB3 inhibitor.

In still another aspect, a method of treating a breast cancer tumor in a patient is provided, the method comprising:

selecting a patient with a TN or BL breast cancer tumor; and administering to the patient an effective amount of an ErbB3 inhibitor.

In another aspect, the patient with a TN or BL breast cancer tumor is a patient further selected by use of the selection methods disclosed in pending international application PCT/US2009/054051.

Identification of a triple negative breast cancer cells, or a patient having a triple negative breast cancer tumor, can be achieved through standard methods well known in the art. For example, immunohistochemical (IHC) staining is routinely used in biopsy analysis and permits the detection, localization and relative quantification of ER, PR, and HER2 within sections from formalin-fixed, paraffin-embedded tissues (e.g., breast cancer tissues routinely processed for histological evaluation). In the context of identifying TN tumors, staining of less than 5% of tumor cell nuclei is considered negative for each of for ER and PR. The primary antibody used for IHC staining of ER is e.g., 1D5 (Chemicon, Temecula Calif., catalog # IHC2055). The primary antibody used for IHC staining of PR is e.g., PgR636 (Thermo Fisher Scientific, Fremont, Calif., catalog # MS-1882-R7) or PgR 1294 (Dako North America, Inc., Carpinteria, Calif., Code M3568). The ErbB2 IHC assay used is e.g., the HercepTest™ Kit (Dako North America, Inc., Carpinteria, Calif., Code K5204), a semi-quantitative IHC assay using a polyclonal anti-HER2 primary antibody to determine HER2 protein overexpression in breast cancer tissues routinely processed for histological evaluation, which is used according to the manufacturer's directions. In the context of identifying TN tumors, a test result of 0 to 1+ is considered Her2 negative.

In one embodiment, the triple negative breast cancer tumor is histopathologically characterized as having a basal-like phenotype. In another embodiment, the triple negative breast cancer tumor is histopathologically characterized as having a phenotype other than basal-like. Examples of TN breast cancer histopathological phenotypes that are other than BL include high grade invasive ductal carcinoma of no special type, metaplastic carcinomas, medullary carcinomas and salivary gland-like tumors of the breast.

In one aspect, the TN or BL breast cancer to be treated with ErbB3 inhibitor coexpresses ErbB1 (EGFR), ErbB3, and heregulin (HRG). Expression of EGFR and HRG can be identified by RT-PCR or by standard immunoassay techniques, such as ELISA assay or immunohistochemical staining of formalin-fixed, paraffin-embedded tissues (e.g., breast cancer tissues routinely processed for histological evaluation), using an anti-EGFR antibody, anti-ErbB3 antibody or an anti-HRG antibody. Additional characteristics of tumors for treatment in accordance with the disclosure herein are set forth in pending U.S. Patent Publication No. 20110027291, which claims priority to PCT application No. PCT/US2009/054051.

In one embodiment, the ErbB3 inhibitor administered to the patient is an anti-ErbB3 antibody. An exemplary anti-ErbB3 antibody is MM-121, comprising $V_H$ and $V_L$ sequences as shown in SEQ ID NOs: 1 and 2, respectively, or an antibody comprising $V_H$ CDR1, 2 and 3 sequences as shown in SEQ ID NOs: 3-5, respectively, and $V_L$ CDR1, 2 and 3 sequences as shown in SEQ ID NOs: 6-8, respectively (i.e., the $V_H$ and $V_L$ CDRs of MM-121). Additional non-limiting exemplary anti-ErbB3 antibodies and other forms of ErbB3 inhibitors are described in detail in Subsection I above.

The ErbB3 inhibitor can be administered to the patient by any route suitable for the effective delivery of the inhibitor to the patient. For example, many small molecule inhibitors are suitable for oral administration. Antibodies and other biologic agents typically are administered parenterally, e.g., intravenously, intraperitoneally, subcutaneously or intramuscularly. Various routes of administration, dosages and pharmaceutical formulations suitable for use in the methods provided herein are described in further detail below.

III. Pharmaceutical Compositions

In another aspect, pharmaceutical compositions are provided that can be used in the methods disclosed herein, i.e., pharmaceutical compositions for treating TN or BL breast cancer tumors.

In one embodiment, the pharmaceutical composition for treating TN breast cancer comprises an ErbB3 inhibitor and a pharmaceutical carrier. The ErbB3 inhibitor can be formulated with the pharmaceutical carrier into a pharmaceutical composition. Additionally, the pharmaceutical composition can include, for example, instructions for use of the composition for the treatment of patients for TN or BL breast cancer tumors.

In one embodiment, the ErbB3 inhibitor in the composition is an anti-ErbB3 antibody, e.g., MM-121 or an antibody comprising the $V_H$ and $V_L$ CDRs of MM-121 positioned in the antibody in the same relative order as they are present in MM-121 so as to provide immunospecific binding of ErbB3. Additional non-limiting exemplary anti-ErbB3 antibodies and other forms of ErbB3 inhibitors are described in detail in Subsection I above.

As used herein, "pharmaceutically acceptable carrier" includes any and all solvents, dispersion media, coatings, antibacterial and antifungal agents, isotonic and absorption delaying agents, buffers, and other excipients that are physiologically compatible. Preferably, the carrier is suitable for parenteral, oral, or topical administration. Depending on the route of administration, the active compound, e.g., small molecule or biologic agent, may be coated in a material to protect the compound from the action of acids and other natural conditions that may inactivate the compound.

Pharmaceutically acceptable carriers include sterile aqueous solutions or dispersions and sterile powders for the extemporaneous preparation of sterile injectable solutions or dispersion, as well as conventional excipients for the preparation of tablets, pills, capsules and the like. The use of such media and agents for the formulation of pharmaceutically active substances is known in the art. Except insofar as any conventional media or agent is incompatible with the active compound, use thereof in the pharmaceutical compositions provided herein is contemplated. Supplementary active compounds can also be incorporated into the compositions.

A pharmaceutically acceptable carrier can include a pharmaceutically acceptable antioxidant. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers which may be employed in the pharmaceutical compositions provided herein include water, ethanol, polyols (such as glycerol, propylene glycol, polyethylene glycol, and the like), and suitable mixtures thereof, and injectable organic esters, such as ethyl oleate. When required, proper fluidity can be maintained, for example, by the use of coating materials, such as lecithin, by the maintenance of the required particle size in the case of dispersions, and by the use of surfactants. In many cases, it will be useful to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

These compositions may also contain functional excipients such as preservatives, wetting agents, emulsifying agents and dispersing agents.

Therapeutic compositions typically must be sterile, non-pyrogenic, and stable under the conditions of manufacture and storage. The composition can be formulated as a solution, microemulsion, liposome, or other ordered structure suitable to high drug concentration.

Sterile injectable solutions can be prepared by incorporating the active compound in the required amount in an appropriate solvent with one or a combination of ingredients enumerated above, as required, followed by sterilization, e.g., by microfiltration. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation include vacuum drying and freeze-drying (lyophilization) that yield a powder of the active ingredient plus any additional desired ingredient from a previously sterile-filtered solution thereof. The active agent(s) may be mixed under sterile conditions with additional pharmaceutically acceptable carrier(s), and with any preservatives, buffers, or propellants which may be required.

Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutical compositions comprising an ErbB3 inhibitor can be administered alone or in combination therapy. For example, the combination therapy can include a composition provided herein comprising an ErbB3 inhibitor and at least one or more additional therapeutic agents, such as one or more chemotherapeutic agents known in the art, discussed in further detail in Subsection IV below. Pharmaceutical compositions can also be administered in conjunction with radiation therapy and/or surgery.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation.

Exemplary dosage ranges for administration of an antibody include: 10-1000 mg (antibody)/kg (body weight of the patient), 10-800 mg/kg, 10-600 mg/kg, 10-400 mg/kg, 10-200 mg/kg, 30-1000 mg/kg, 30-800 mg/kg, 30-600 mg/kg, 30-400 mg/kg, 30-200 mg/kg, 50-1000 mg/kg, 50-800 mg/kg, 50-600 mg/kg, 50-400 mg/kg, 50-200 mg/kg, 100-1000 mg/kg, 100-900 mg/kg, 100-800 mg/kg, 100-700 mg/kg, 100-600 mg/kg, 100-500 mg/kg, 100-400 mg/kg, 100-300 mg/kg and 100-200 mg/kg. Exemplary dosage schedules include once every three days, once every five days, once every seven days (i.e., once a week), once every 10 days, once every 14 days (i.e., once every two weeks), once every 21 days (i.e., once every three weeks), once every 28 days (i.e., once every four weeks) and once a month.

It may be advantageous to formulate parenteral compositions in unit dosage form for ease of administration and uniformity of dosage. Unit dosage form as used herein refers to physically discrete units suited as unitary dosages for the patients to be treated; each unit contains a predetermined quantity of active agent calculated to produce the desired therapeutic effect in association with any required pharmaceutical carrier. The specification for unit dosage forms are dictated by and directly dependent on (a) the unique characteristics of the active compound and the particular therapeutic effect to be achieved, and (b) the limitations inherent in the art of compounding such an active compound for the treatment of sensitivity in individuals.

Actual dosage levels of the active ingredients in the pharmaceutical compositions disclosed herein may be varied so as to obtain an amount of the active ingredient which is effective to achieve the desired therapeutic response for a particular patient, composition, and mode of administration, without being toxic to the patient. "Parenteral" as used herein in the context of administration means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The phrases "parenteral administration" and "administered parenterally" as used herein refer to modes of administration other than enteral (i.e., via the digestive tract) and topical administration, usually by injection or infusion, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Intravenous injection and infusion are often (but not exclusively) used for antibody administration.

When agents provided herein are administered as pharmaceuticals, to humans or animals, they can be given alone or as a pharmaceutical composition containing, for example, 0.001 to 90% (e.g., 0.005 to 70%, e.g., 0.01 to 30%) of active ingredient in combination with a pharmaceutically acceptable carrier.

IV. Combination Therapy

In certain embodiments, the methods and uses provided herein for suppressing growth of TN breast cancer cells or for treating a patient with a TN breast tumor or BL breast tumor can comprise administration of an ErbB3 inhibitor and at least one additional anti-cancer agent that is not an ErbB3 inhibitor.

In one embodiment, the at least one additional anti-cancer agent comprises at least one chemotherapeutic drug. Non-limiting examples of such chemotherapeutic drugs include platinum-based chemotherapy drugs (e.g., cisplatin, carboplatin), taxanes (e.g., paclitaxel (Taxol®), docetaxel (Taxotere®), EndoTAG-1™ (a formulation of paclitaxel encapsulated in positively charged lipid-based complexes; MediGene), Abraxane® (a formulation of paclitaxel bound to albumin)), tyrosine kinase inhibitors (e.g., imatinib/Gleevec®, sunitinib/Sutent®, dasatinib/Sprycel®), and combinations thereof.

In another embodiment, the at least one additional anti-cancer agent comprises an EGFR inhibitor, such as an anti-EGFR antibody or a small molecule inhibitor of EGFR signaling. An exemplary anti-EGFR antibody is cetuximab (Erbitux®). Cetuximab is commercially available from ImClone Systems Incorporated. Other examples of anti-EGFR antibodies include matuzumab (EMD72000), panitumumab (Vectibix®; Amgen); nimotuzumab (TheraCIM™) and mAb 806. An exemplary small molecule inhibitor of the EGFR signaling pathway is gefitinib (Iressa®), which is commercially available from AstraZeneca and Teva. Other examples of small molecule inhibitors of the EGFR signaling pathway include erlotinib HCL (OSI-774; Tarceva®, OSI Pharma); lapatinib (Tykerb®, GlaxoSmithKline); canertinib (canertinib dihydrochloride, Pfizer); pelitinib (Pfizer); PKI-166 (Novartis); PD158780; and AG 1478 (4-(3-Chloroanillino)-6,7-dimethoxyquinazoline).

In yet another embodiment, the at least one additional anti-cancer agent comprises a VEGF inhibitor. An exemplary VEGF inhibitor comprises an anti-VEGF antibody, such as bevacizumab (Avastatin®; Genentech).

In still another embodiment, the at least one additional anti-cancer agent comprises an anti-ErbB2 antibody. Suitable anti-ErbB2 antibodies include trastuzumab and pertuzumab.

In one aspect, the improved effectiveness of a combination according to the invention can be demonstrated by achieving therapeutic synergy.

The term "therapeutic synergy" is used when the combination of two products at given doses is more efficacious than the best of each of the two products alone at the same doses. In one example, therapeutic synergy can be evaluated by comparing a combination to the best single agent using estimates obtained from a two-way analysis of variance with repeated measurements (e.g., time factor) on parameter tumor volume.

The term "additive" refers to when the combination of two or more products at given doses is equally efficacious than the sum of the efficacies obtained with of each of the two or more products, whilst the term "superadditive" refers to when the combination is more efficacious than the sum of the efficacies obtained with of each of the two or more products.

Another measure by which effectiveness (including effectiveness of combinations) can be quantified is by calculating the $\log_{10}$ cell kill, which is determined according to the following equation:

$$\log_{10} \text{ cell kill} = T - C(\text{days}) / 3.32 \times T_d$$

in which T-C represents the delay in growth of the cells, which is the average time, in days, for the tumors of the treated group (T) and the tumors of the control group (C) to have reached a predetermined value (1 g, or 10 mL, for example), and $T_d$ represents the time, in days necessary for the volume of the tumor to double in the control animals. When applying this measure, a product is considered to be active if $\log_{10}$ cell kill is greater than or equal to 0.7 and a product is considered to be very active if $\log_{10}$ cell kill is greater than 2.8.

Using this measure, a combination, used at its own maximum tolerated dose, in which each of the constituents is present at a dose generally less than or equal to its maximum tolerated dose, exhibits therapeutic synergy when the $\log_{10}$ cell kill is greater than the value of the $\log_{10}$ cell kill of the best constituent when it is administered alone. In an exemplary case, the $\log_{10}$ cell kill of the combination exceeds the value of the $\log_{10}$ cell kill of the best constituent of the combination by at least one log cell kill

EXAMPLES

Example 1

MM-121 Effects on Triple Negative Human Breast Cancer Xenograft MAXF449

An analysis of the anti-tumor efficacy and tolerability of MM-121 treatment of tumor-bearing mice is carried out using triple negative human mammary carcinoma xenograft MAXF449 (ONCOTEST GmbH, Frieburg, Germany) in NMRI nude mice. MAXF449 is a Human tumor explant (histologically described upon explant as solid invasive ductal, and poorly defined) established via subcutaneous injection in serial passages in nude mice. The MAXF449 cells used in these experiments have been passaged 22 times. NMRI nude mice are obtained from Taconic farms, Charles River Laboratories International, or Harlan Laboratories. The mice are housed in Tecniplast Individually Ventilated polycarbonate (Macrolon) Cages (IVC) set in climate-controlled rooms and have free access to food and acidified water.

To investigate anti-tumor efficacy in monotherapy, MM-121 or vehicle control (100 µL) is given to tumor-bearing mice at 600 µg per mouse (MM-121 as a 6 mg/mL solution in PBS) by IP injection every three days. Control mice receive the PBS vehicle only. Efficacy is determined by comparing tumor growth between the antibody-treated mice and the vehicle control mice and is expressed as the experimental to control ratio of median relative tumor volumes (T/C value). A minimum T/C value below 50% is a prerequisite for rating a treatment as effective. The control and experimental groups each contain 10 mice bearing one tumor each. To obtain 30 mice bearing tumors of similar sizes for randomization, 40 mice per tumor are implanted unilaterally.

Mice are randomized and therapy begins when a sufficient number of individual tumors have grown to a volume of approximately 200 mm3. Tumors are measured (L×W) by digital caliper measurement and the tumor volume is calculated using the formula Pi/6 (W2×L). The first dose is administered either on Day 0 (day of randomization) or one day later.

Approximately 24 hours after administration of the final dose all mice are bled to prepare serum; in addition, tumors are collected from the same mice for flash-freezing and FFPE (1/2 tumor each).

According to regulations for animal experiments, mice are sacrificed if the tumor volume exceeds 1800 mm³ (one tumor per mouse). Mice are monitored and dosed until their tumors have grown to that size but no longer than 60 days. Thereafter, they are sacrificed for sample collection.

At the end of the study, approximately 24 hours after administration of the final dose, all mice on study are bled sublingually to obtain a maximum amount of blood for the preparation of serum. Serum is aliquoted in 2 tubes with approximately 250 µL in each.

In addition, tumors from all mice are excised without delay for snap-freezing in liquid nitrogen (1/2 tumor, COVARIS bags for the storage of samples are provided) and for fixation in 10% buffered formalin for <24 hours, subsequent dehydration and paraffin embedding (FFPE, 1/2 tumor).

Animal weights and tumor diameters (W and L) are measured twice weekly and tumor volumes are calculated using the formula Pi/6 (W2×L). Tumor growth curves are plotted. Tumor inhibition and absolute growth delay for 2 and 4 doubling times are calculated.

Results of experiments that were carried out substantially as described are presented in FIG. 1. MM-121 treatment inhibited or stopped tumor growth, and in some cases reduced tumor size. TGI (tumor growth inhibition) in these human triple negative tumor xenografts was calculated to be approximately 200%.

Example 2

MM-121 Effects on Triple-Negative Human Breast Cancer Xenograft MDA-MB-231

Balb/c nude mice are injected under general anesthesia with $10^7$ MDA-MB-231 human triple negative breast cancer cells (ATCC) either subcutaneously in the flank or into the mammary fat pad. Mice with established tumors (i.e., after 7-10 days of tumor growth following injection of cells) are then treated IP with either PBS or MM-121 every 3 days with 600 ug MM-121 per mouse as described in Example 1. Tumor volume is measured twice a week as described in Example 1.

Figure 2:
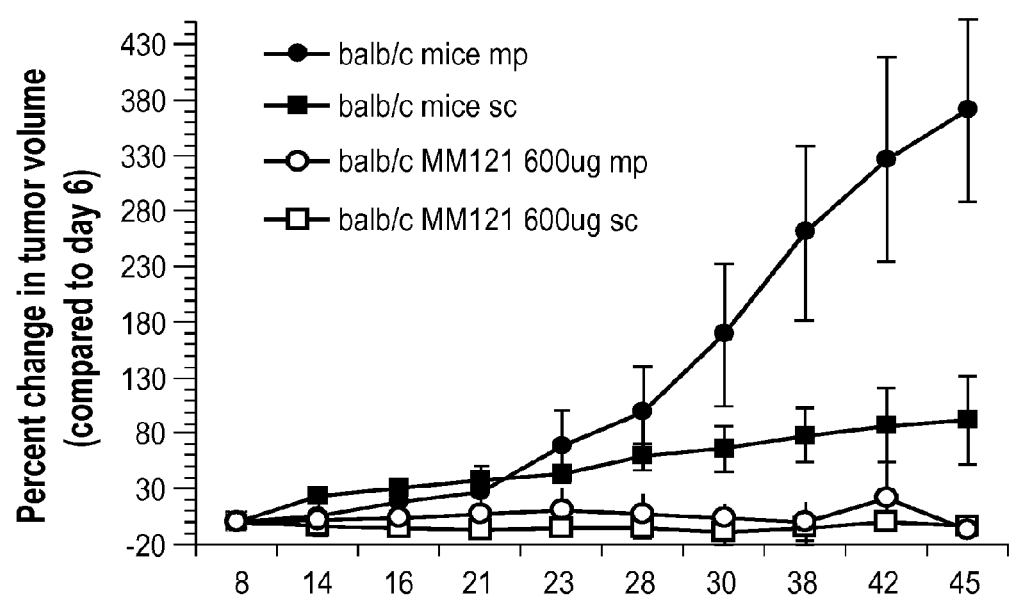
FIG. 2 is a graph showing the percent change in MDA-MB-231 xenograft tumor volume (Y axis—normalized to initial tumor volume) plotted against time in days following injection of MDA-MB-231 cells (X axis) in Balb/c nude mice treated with MM-121 or vehicle control. Curves with open timepoint squares or circles indicate mice treated with MM-121. Curves with filled timepoint squares or circles indicate vehicle controls. In the inset, "mp" indicates that the MDA-MB-231 cells were injected into the mammary fat pad, while "sc" indicates that the MDA-MB-231 cells were injected subcutaneously in the flank.

Results of experiments carried out substantially as described are presented in FIG. 2. MM-121 treatment stopped human triple negative breast cancer tumor growth essentially completely in these experiments.

Example 3

Measurement of Binding Affinity ($K_D$)

The dissociation constants of anti-ErbB antibodies may be measured using either or both of two independent techniques, a Surface Plasmon Resonance Assay and a cell binding assay.

Surface Plasmon Resonance Assay

The Surface Plasmon Resonance Assay is performed as described in Wassaf et al. (2006) *Analytical Biochem.*, 351:241-253. One implementation uses a BIACORE 3000 instrument (GE Healthcare) using a recombinant ErbB protein as the analyte and the anti-ErbB antibody as the ligand The $K_D$ value is calculated based on the formula $K_D=K_d/K_a$.

Cell Binding Assay

A cell binding assay is performed using MALME-3M cells (ATCC) for ErbB3 binding. The assay is performed substantially as follows.

Cells are detached with 2 mLs trypsin-EDTA+2 mLs RMPI+5 mM EDTA at room temperature for 5 minutes. Complete RPMI (10 mLs) is added immediately to the trypsinized cells, resuspended gently and spun down in a Beckman tabletop centrifuge at 1100 rpm for 5 minutes. Cells are resuspended in BD stain buffer (PBS+2% FBS+ 0.1% sodium azide, Becton Dickinson) at a concentration of $2\times10^6$ cells per ml and 50 µl ($1\times10^5$ cells) aliquots are plated in a 96-well titer plate.

A 150 µl solution of 200 nM anti-ErbB antibody in BD stain buffer is prepared and serially diluted 2-fold into 75 µl BD stain buffer. The concentrations of the diluted antibody ranged from 200 nM to 0.4 nM. 50 µl aliquots of the different protein dilutions are then added directly to the 50 ul cell suspension giving the final concentrations of 100 nM, 50 nM, 25 nM, 12 nM, 6 nM, 3 nM, 1.5 nM, 0.8 nM, 0.4 nM and 0.2 nM of the antibody.

Aliquoted cells in the 96-well plate are incubated with the protein dilutions for 30 minutes at room temperature on a platform shaker and washed 3 times with 300 µl BD stain buffer. Cells are then incubated with 100 µl of secondary antibody (e.g., a 1:750 dilution of Alexa 647-labeled goat anti-human IgG in BD stain buffer) for 45 minutes on a platform shaker in the cold room. Finally, cells are washed twice, pelleted and resuspended in 250 µl BD stain buffer+ 0.5 µg/ml propidium iodide. Analysis of 10,000 cells is done in a FACSCALIBUR flow cytometer using the FL4 channel. MFI values and the corresponding concentrations of the anti-ErbB-antibody are plotted on the y-axis and x-axis, respectively. The $K_D$ of the molecule is determined using GraphPad PRISM software using the one-site binding model for a non-linear regression curve.

The $K_D$ value is calculated based on the formula $Y=Bmax*X/K_D+X$ (Bmax=fluorescence at saturation. X=antibody concentration. Y=degree of binding).

Example 4

Inhibition of Tumor Growth In Vivo by Combination Treatment with MM-121 and Paclitaxel Methods:

Balb/c nude mice (female, 4-5 weeks old from Charles River lab) are implanted orthotopically with 10×106 cells in mammary pad. Tumors are allowed to reach average of 100 mm³ in size before randomization into 4 groups of 10 mice, containing mice with a similar size distribution of tumors. Each group of mice is treated with 1) MM-121 (150 ug/mouse, ip., Q3D) or 2) vehicle control (PBS, ip.) or 3) paclitaxel (5 mg/kg LC Labs) or 4) paclitaxel (5 mg/kg) and MM-121 (150 ug/mouse). Treatment is continued for 4 weeks. Tumors are measured twice weekly and tumor volume is calculated as p/6×length×width, where the width is the shorter measurement.

Figure 3:
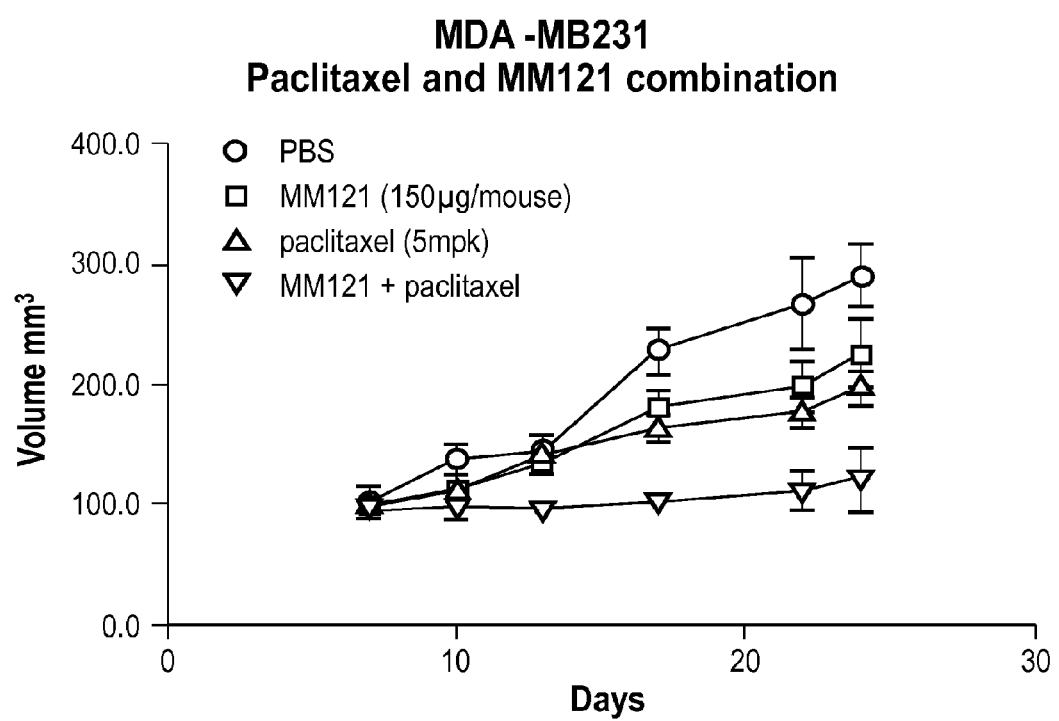
FIG. 3 is a graph showing MDA-MB-231 tumor volume in mm$^3$ (Y axis) plotted against time in days (X-axis) starting at 28 days following injection of MDA-MB-231 cells into the mammary fat pads of Balb/c nude mice. Treatment was with MM-121 (150 µg/mouse), paclitaxel (5 mg/kg), a combination of MM-121 (150 µg/mouse) and paclitaxel (5 mg/kg), or vehicle control. Where used in the figures, "mpk"=mg/kg.

Results:

The combination of MM-121 with paclitaxel was investigated in vivo in the MDA-MB-231 triple negative breast cancer xenograft model using the methods described above or minor variations thereof. Mice were treated with sub-optimal doses of MM-121, paclitaxel, a combination of MM-121 and paclitaxel, or vehicle control (FIG. 3). While both MM-121 and paclitaxel each inhibited tumor growth in vivo, mice receiving a combination therapy of MM-121 and paclitaxel exhibited an improvement of tumor growth inhibition when compared to that obtained with each of the individual treatments. The improvement in tumor growth inhibition exhibited therapeutic synergy and was at least about additive as compared to the improvement obtained with each of the single agents of the combination.

Table 1 shows data used to generate FIG. 3. Table 2 shows the mean % change in tumor volumes using data from the same experiments shown in FIG. 3, normalized to initial tumor volume.

TABLE 1 data used to generate FIG. 3 - mean tumor volumes in $mm^3$

| | | | | | | | |
|---|---|---|---|---|---|---|---|
| Vehicle | Mean | 104.4 | 137.1 | 144.5 | 229.5 | 253.7 | 291.0 |
| MM121 150 μg | Mean | 99.4 | 115.5 | 137.5 | 180.4 | 187.2 | 242.7 |
| paclitaxel 5 mg/kg | Mean | 97.9 | 113.5 | 144.6 | 166.2 | 178.8 | 202.2 |
| MM121 150 μg + paclitaxel 5 mg/kg | Mean | 96.2 | 100.8 | 98.3 | 104.1 | 113.0 | 121.6 |

Example 5

MM-121 Combination with Targeted and Chemotherapies In Vivo

Methods:

Balb/c nude mice (female, 4-5 weeks old from Charles River lab) are implanted orthotopically with 10×106 cells in mammary pad. Tumors are allowed to reach average of 150 $mm^3$ in size before randomization into 9 groups of 8 mice, containing mice with a similar size distribution of tumors. Each group of mice is treated with a dose of 1) MM-121 (300 ug/mouse, ip., Q3D) or 2) vehicle control (PBS, ip.) or 3) paclitaxel (10 mg/kg LC Labs) or 4) erlotinib (50 mg/kg PO 5XQD) or 5) cetuximab (2 mg/kg Q3D) or combination therapy with: 6) erlotinib (50 mg/kg) and MM-121 (300 ug/mouse), or 7) cetuximab (2 mg/kg) and MM-121 (300 ug/mouse), or 8) erlotinib (50 mg/kg) and MM-121 (300 ug/mouse) and paclitaxel (10 mg/kg), or 9) cetuximab (2 mg/kg) and MM121 (300 ug/mouse) and paclitaxel (10 mg/kg). Treatment is continued for 4 weeks. Tumors are measured twice weekly and tumor volume is calculated as p/6×length×width, where the width is the shorter measurement.

Figure 4A:
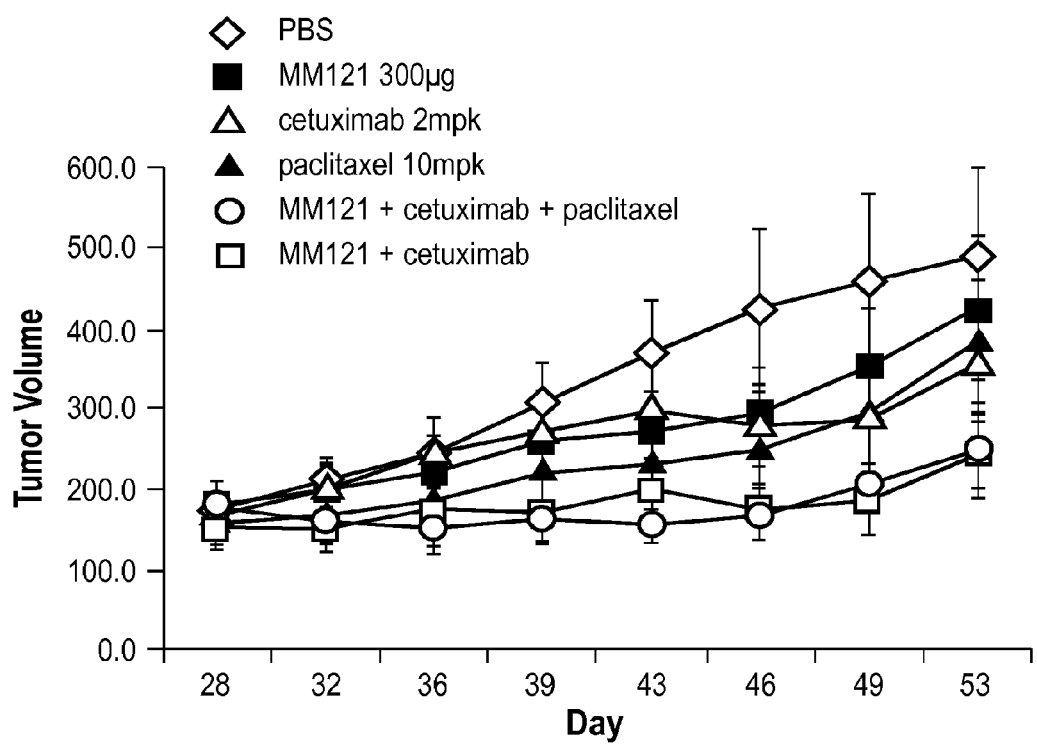
FIGS. 4A and 4B present graphs showing MDA-MB-231 tumor volume in mm$^3$ (Y axis) plotted against time in days (X-axis) starting at 28 days following injection of MDA-MB-231 cells into the mammary fat pads of Balb/c nude mice.
Figure 4B:
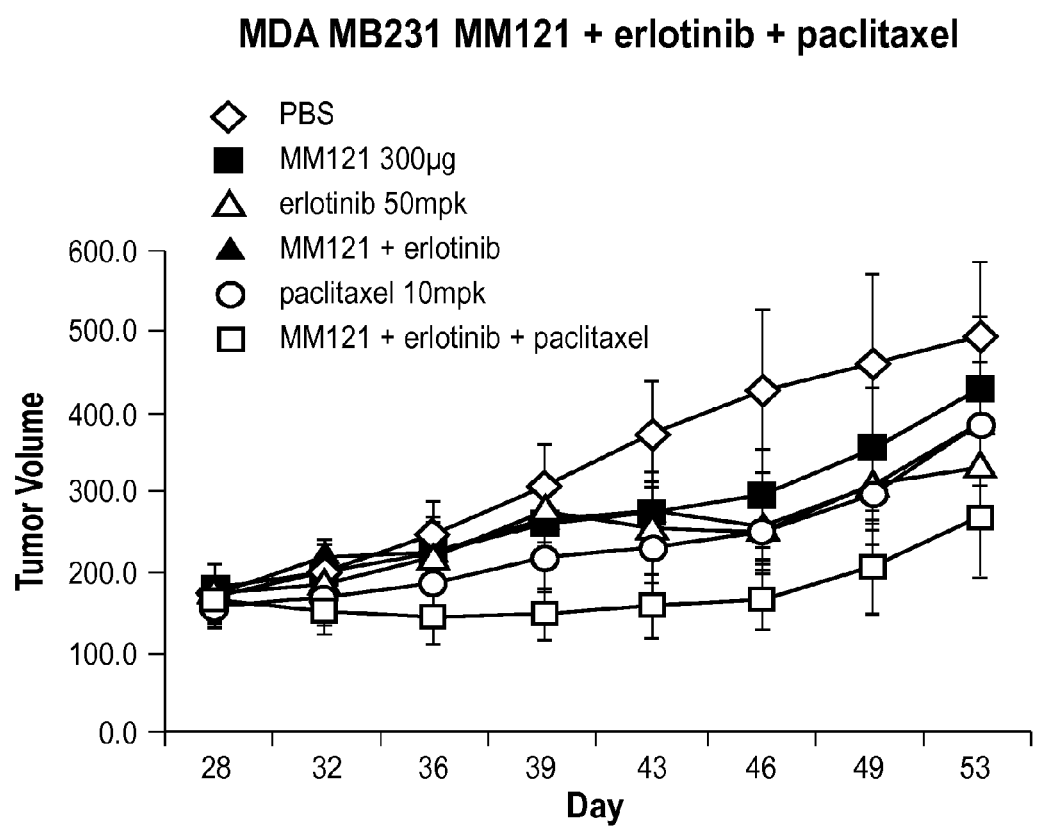

Results: In order to test the efficacy of MM-121 to inhibit tumor growth when used in combination with other agents, these combinations were tested in vivo in the MDA-MB-231 triple negative breast cancer xenograft model using the methods described above or minor variations thereof. Mice were treated with MM-121 (administered at sub-optimal doses in the combinations), cetuximab, paclitaxel, MM-121 and cetuximab, and the triple combination MM-121 and cetuximab and paclitaxel. As shown in FIG. 4A, combination therapy with MM-121 and cetuximab inhibited tumor growth to a greater extent than either agent alone and essentially stopped tumor growth until at least day 39. The decreased rate of growth showed therapeutic synergy and, in certain cases represented at least about an additive decrease in growth compared to the decreased rates obtained with any of the single therapies. Addition of paclitaxel did not enhance the effect of MM-121 and cetuximab. Mice were then treated with MM-121, erlotinib, MM-121 and erlotinib, or the triple combination of MM-121 and erlotinib and paclitaxel. As shown in FIG. 4B, MM-121 in combination with erlotinib did not have a statistically significant effect on the rate of tumor growth compared with treatment with either agent alone. Conversely, treatment with the triple combination of MM-121, erlotinib, and paclitaxel resulted in a clearly decreased rate of tumor growth and essentially stopped tumor growth until at least day 39. The decreased rate of growth showed therapeutic synergy and, in certain cases represented at least about an additive decrease in growth compared to the decreased rates obtained with any of the single or double therapies.

Table 3 shows data used to generate FIGS. 4A and 4B. Table 4 shows the mean % change in tumor volume using data from the same experiments shown in FIGS. 4A and 4B, normalized to initial tumor volume.

TABLE 2

Data used to generate FIGS. 4A and 4B - mean tumor volumes in $mm^3$.

| | Day | | | | | | | |
|---|---|---|---|---|---|---|---|---|
| | 28 | 32 | 36 | 39 | 43 | 46 | 49 | 53 |
| PBS | 163.7 | 199.0 | 242.8 | 304.5 | 369.4 | 423.4 | 458.4 | 490.7 |
| MM121 300 ug | 178.6 | 197.3 | 219.1 | 257.8 | 269.4 | 291.4 | 351.3 | 425.0 |
| erlotinib 50 mg/kg | 172.1 | 182.1 | 216.1 | 273.2 | 252.8 | 245.6 | 303.1 | 327.4 |
| cetuximab 2 mg/kg | 172.4 | 210.6 | 245.0 | 269.2 | 296.3 | 279.7 | 283.5 | 358.1 |
| MM121 + erlotinib | 170.6 | 215.5 | 221.8 | 261.7 | 272.5 | 255.3 | 305.2 | 378.3 |
| paclitaxel 10 mg/kg | 155.2 | 167.0 | 182.4 | 216.6 | 228.1 | 247.0 | 292.6 | 383.5 |
| MM121 + cetuximab | 152.5 | 149.6 | 171.6 | 169.1 | 196.6 | 171.2 | 182.9 | 241.2 |
| MM121 + erlotinib + paclitaxel | 164.8 | 149.3 | 139.8 | 146.5 | 156.7 | 163.4 | 202.9 | 264.5 |
| MM121 + cetuximab + paclitaxel | 176.3 | 158.5 | 147.8 | 160.4 | 154.4 | 163.4 | 203.4 | 247.7 |

Equivalents

Those skilled in the art will recognize, or be able to ascertain using no more than routine experimentation, many equivalents of the specific embodiments described herein. Such equivalents are intended to be encompassed by the following claims. Any combinations of the embodiments disclosed in the dependent claims are contemplated to be within the scope of the invention.

INCORPORATION BY REFERENCE

Each and every, issued patent, patent application and publication referred to herein is hereby incorporated herein by reference in its entirety.

SUMMARY OF SEQUENCE LISTING

MM-121 $V_H$ amino acid sequence (SEQ ID NO: 1)
EVQLLESGGGLVQPGGSLRLSCAASGFTFSHYVMAWVRQAPGKGLEWVSSISSSGG
WTLYADSVKGRFTISRDNSKNTLYLQMNSLRAEDTAVYYCTRGLKMATIFDYWGQ
GTLVTVSS MM-121 $V_L$ amino acid sequence (SEQ ID NO: 2)
QSALTQPASVSGSPGQSITISCTGTSSDVGSYNVVSWYQQHPGKAPKLIIYEVSQRPSG
VSNRFSGSKSGNTASLTISGLQTEDEADYYCCSYAGSSIFVIFGGGTKVTVL

MM-121 $V_H$ CDR1 (SEQ ID NO: 3)
HYVMA

MM-121 $V_H$ CDR2 (SEQ ID NO: 4)
SISSSGGWTLYADSVKG

MM-121 $V_H$ CDR3 (SEQ ID NO: 5)
GLKMATIFDY

MM-121 $V_L$ CDR1 (SEQ ID NO: 6)
TGTSSDVGSYNVVS

MM-121 $V_L$ CDR2 (SEQ ID NO: 7)
EVSQRPS

MM-121 $V_L$ CDR3 (SEQ ID NO: 8)
CSYAGSSIFVI

Ab #3 $V_H$ amino acid sequence (SEQ ID NO: 9)
EVQLLESGGGLVQPGGSLRLSCAASGFTFSAYNMRWVRQAPGKGLEWVSVIYPSGG
ATRYADSVKGRFTISRDNSKNTLYLQMNSLRAEDTAVYYCARGYYYYGMDVWGQ
GTLVTVSS Ab #3 $V_L$ amino acid sequence (SEQ ID NO: 10)
QSVLTQPPSASGTPGQRVTISCSGSDSNIGRNYIYWYQQFPGTAPKLLIYRNNQRPSG
VPDRISGSKSGTSASLAISGLRSEDEAEYHCGTWDDSLSGPVFGGGTKLTVL Ab # 3 $V_H$ CDR1 (SEQ ID NO: 11)
AYNMR Ab # 3 $V_H$ CDR2 (SEQ ID NO: 12)
VIYPSGGATRYADSVKG Ab # 3 $V_H$ CDR3 (SEQ ID NO: 13)
GYYYYGMDV Ab # 3 $V_L$ CDR1 (SEQ ID NO: 14)
SGSDSNIGRNYIY Ab # 3 $V_L$ CDR2 (SEQ ID NO: 15)
RNNQRPS Ab # 3 $V_L$ CDR3 (SEQ ID NO: 16)
GTWDDSLSGPV Ab # 14 $V_H$ amino acid sequence (SEQ ID NO: 17)
EVQLLESGGGLVQPGGSLRLSCAASGFTFSAYGMGWVRQAPGKGLEWVSYISPSGG
HTKYADSVKGRFTISRDNSKNTLYLQMNSLRAEDTAVYYCAKVLETGLLVDAFDIVV
GQGTMVTVSS Ab # 14 $V_L$ amino acid sequence (SEQ ID NO: 18)
QYELTQPPSVSVYPGQTASITCSGDQLGSKFVSWYQQRPGQSPVLVMYKDKRRPSEI
PERFSGSNSGNTATLTISGTQAIDEADYYCQAWDSSTYVFGTGTKVTVL Ab # 14 $V_H$ CDR1 (SEQ ID NO: 19)
AYGMG Ab # 14 $V_H$ CDR2 (SEQ ID NO: 20)
YISPSGGHTKYADSVKG Ab # 14 $V_H$ CDR3 (SEQ ID NO: 21)
VLETGLLVDAFDI Ab # 14 $V_L$ CDR1 (SEQ ID NO: 22)
SGDQLGSKFVS Ab # 14 $V_L$ CDR2 (SEQ ID NO: 23)
YKDKRRPS

SUMMARY OF SEQUENCE LISTING

Ab # 14 V<sub>L</sub> CDR3 (SEQ ID NO: 24)
QAWDSSTYV

Ab # 17 V<sub>H</sub> amino acid sequence (SEQ ID NO: 25)
EVQLLESGGGLVQPGGSLRLSCAASGFTFSWYGMGWVRQAPGKGLEWVSYISPSGG
ITVYADSVKGRFTISRDNSKNTLYLQMNSLRAEDTAVYYCARLNYYYGLDVWGQG
TTVTVSS Ab # 17 V<sub>L</sub> amino acid sequence (SEQ ID NO: 26)
QDIQMTQSPSSLSASVGDRITITCQASQDIGDSLNWYQQKPGKAPRLLIYDASNLETG
VPPRFSGSGSGTDFTFTFRSLQPEDIATYFCQQSANAPFTFGPGTKVDIK Ab # 17 V<sub>H</sub> CDR1 (SEQ ID NO: 27)
WYGMG Ab # 17 V<sub>H</sub> CDR2 (SEQ ID NO: 28)
YISPSGGITVYADSVKG Ab # 17 V<sub>H</sub> CDR3 (SEQ ID NO: 29)
LNYYYGLDV Ab # 17 V<sub>L</sub> CDR1 (SEQ ID NO: 30)
QASQDIGDSLN Ab # 17 V<sub>L</sub> CDR2 (SEQ ID NO: 31)
DASNLET Ab # 17 V<sub>L</sub> CDR3 (SEQ ID NO: 32)
QQSANAPFT Ab # 19 V<sub>H</sub> amino acid sequence (SEQ ID NO: 33)
EVQLLESGGGLVQPGGSLRLSCAASGFTFSRYGMWWVRQAPGKGLEWVSYIGSSGG
PTYYVDSVKGRFTISRDNSKNTLYLQMNSLRAEDTAVYYCAGGRGTPYYFDSWGQ
GTLVTVSS Ab # 19 V<sub>L</sub> amino acid sequence (SEQ ID NO: 34)
QYELTQPASVSGSPGQSITISCTGTSSDIGRWNIVSWYQQHPGKAPKLMIYDVSNRPS
GVSNRF
SGSKSGNTASLTISGLQAEDEADYYCSSYTSSSTWVFGGGTKLTVL Ab # 19 V<sub>H</sub> CDR1 (SEQ ID NO: 35)
RYGMW Ab # 19 V<sub>H</sub> CDR2 (SEQ ID NO: 36)
YIGSSGGPTYYVDSVKG Ab # 19 V<sub>H</sub> CDR3 (SEQ ID NO: 37)
GRGTPYYFDS Ab # 19 V<sub>L</sub> CDR1 (SEQ ID NO: 38
TGTSSDIGRWNIVS Ab # 19 V<sub>L</sub> CDR2 (SEQ ID NO: 39)
DVSNRPS Ab # 19 V<sub>L</sub> CDR3 (SEQ ID NO: 40)
SSYTSSSTWV ErbB3 (SEQ ID NO: 41)
SEVGNSQAVCPGTLNGLSVTGDAENQYQTLYKLYERCEVVMGNLEIVLTGHNADLS

FLQWIREVTGYVLVAMNEFSTLPLPNLRVVRGTQVYDGKFAIFVMLNYNTNSSHAL

RQLRLTQLTEILSGGVYIEKNDKLCHMDTIDWRDIVRDRDAEIVVKDNGRSCPPCH

EVCKGRCWGPGSEDCQTLTKTICAPQCNGHCFGPNPNQCCHDECAGGCSGPQDTDC

FACRHFNDSGACVPRCPQPLVYNKLTFQLEPNPHTKYQYGGVCVASCPHNFVVDQT

SCVRACPPDKMEVDKNGLKMCEPCGGLCPKACEGTGSGSRFQTVDSSNIDGFVNCT

KILGNLDFLITGLNGDPWHKIPALDPEKLNVFRTVREITGYLNIQSWPPHMHNFSV

FSNLTTIGGRSLYNRGFSLLIMKNLNVTSLGFRSLKEISAGRIYISANRQLCYHHS

LNWTKVLRGPTEERLDIKHNRPRRDCVAEGKVCDPLCSSGGCWGPGPGQCLSCRNY

SUMMARY OF SEQUENCE LISTING

SRGGVCVTHCNFLNGEPREFAHEAECFSCHPECQPMEGTATCNGSGSDTCAQCAHF

RDGPHCVSSCPHGVLGAKGPIYKYPDVQNECRPCHENCTQGCKGPELQDCLGQTLV

LIGKTHLTMALTVIAGLVVIFMMLGGTFLYWRGRRIQNKRAMRRYLERGESIEPLD

PSEKANKVLARIFKETELRKLKVLGSGVFGTVHKGVWIPEGESIKIPVCIKVIEDK

SGRQSFQAVTDHMLAIGSLDHAHIVRLLGLCPGSSLQLVTQYLPLGSLLDHVRQHR

GALGPQLLLNWGVQIAKGMYYLEEHGMVHRNLAARNVLLKSPSQVQVADFGVADLL

PPDDKQLLYSEAKTPIKWMALESIHFGKYTHQSDVWSYGVTVWELMTFGAEPYAGL

RLAEVPDLLEKGERLAQPQICTIDVYMVMVKCWMIDENIRPTFKELANEFTRMARD

PPRYLVIKRESGPGIAPGPEPHGLTNKKLEEVELEPELDLDLDLEAEEDNLATTTL

GSALSLPVGTLNRPRGSQSLLSPSSGYMPMNQGNLGESCQESAVSGSSERCPRPVS

LHPMPRGCLASESSEGHVTGSEAELQEKVSMCRSRSRSRSPRPRGDSAYHSQRHSL

LTPVTPLSPPGLEEEDVNGYVMPDTHLKGTPSSREGTLSSVGLSSVLGTEEEDEDE

EYEYMNRRRRHSPPHPPRPSSLEELGYEYMDVGSDLSASLGSTQSCPLHPVPIIVI

PTAGTTPDEDYEYMNRQRDGGGPGGDYAAMGACPASEQGYEEMRAFQGPGHQAPHV

HYARLKTLRSLEATDSAFDNPDYWHSRLFPKANAQRT

---

We claim:

1. A method of treating a patient having a tumor that expresses ErbB3 and is identified as a triple negative breast cancer, the method comprising administering to the patient an effective amount of an anti-ErbB3 antibody, or antigen-binding fragment thereof, comprising a $V_H$ CDR1 sequence of SEQ ID NO:3, a $V_H$ CDR2 sequence of SEQ ID NO:4 and a $V_H$ CDR3 sequence of SEQ ID NO:5, and a $V_L$ CDR1 sequence of SEQ ID NO:6, a $V_L$ CDR2 sequence of SEQ ID NO:7 and a $V_L$ CDR3 sequence of SEQ ID NO:8, that binds to all or a portion of residues 92-104 of SEQ ID NO:41.

2. The method of claim 1, wherein the anti-ErbB3 antibody binds to the same epitope as an antibody comprising a $V_H$ sequence as shown in SEQ ID NO:1 and a $V_L$ sequence as shown in SEQ ID NO:2.

3. The method of claim 1, wherein administration of the effective amount of the anti-ErbB3 antibody suppresses growth of the triple negative breast cancer tumor.

4. The method of claim 1, wherein the triple negative breast cancer is histopathologically characterized as having a basal-like phenotype.

5. The method of claim 1, wherein the triple negative breast cancer is histopathologically characterized as having a phenotype other than basal-like.

6. The method of claim 1, which further comprises administering to the patient an effective amount of at least one additional anti-cancer agent.

7. The method of claim 6, wherein the at least one additional anti-cancer agent is selected from the group consisting of platinum-based chemotherapy drugs, taxanes, tyrosine kinase inhibitors, anti-EGFR antibodies, anti-ErbB2 antibodies, and combinations thereof.

8. The method of claim 7, wherein the at least one additional anti cancer agent is a taxane and the taxane is paclitaxel.

9. The method of claim 6, wherein the at least one additional anti-cancer agent comprises an EGFR inhibitor.

10. The method of claim 9, wherein the EGFR inhibitor comprises an anti-EGFR antibody.

11. The method of claim 10, wherein the anti-EGFR antibody is selected from the group consisting of cetuximab, matuzumab, panitumumab, nimotuzumab and mAb 806.

12. The method of claim 9, wherein the EGFR inhibitor is a small molecule inhibitor of EGFR signaling selected from the group consisting of gefitinib, lapatinib, canertinib, pelitinib, and erlotinib HCL.

13. The method of claim 6, wherein the at least one additional anti-cancer agent comprises a VEGF inhibitor.

14. The method of claim 13, wherein the VEGF inhibitor comprises bevacizumab.

15. The method of claim 1, wherein the triple negative breast cancer tumor is a tumor which scores negative for estrogen receptor (ER) and progesterone receptor and yields a test result of 0, 1+, or 2+ using a semi-quantitative immunohistochemical assay using a polyclonal anti-HER2 primary antibody.

16. The method of claim 15, wherein the tumor is FISH negative for HER2 gene amplification.

17. A method of treating a patient having a tumor that expresses ErbB3 and is identified as a triple negative breast cancer which has a basal-like phenotype, the method comprising administering to the patient an effective amount of an anti-ErbB3 antibody, or antigen-binding fragment thereof, comprising a $V_H$ CDR1 sequence of SEQ ID NO:3, a $V_H$ CDR2 sequence of SEQ ID NO:4 and a $V_H$ CDR3 sequence of SEQ ID NO:5, and a $V_L$ CDR1 sequence of SEQ ID NO:6, a $V_L$ CDR2 sequence of SEQ ID NO:7 and a $V_L$ CDR3 sequence of SEQ ID NO:8 that binds to all or a portion of residues 92-104 of SEQ ID NO:41.

18. The method of claim 17, wherein the anti-ErbB3 antibody binds to the same epitope as an antibody comprising a $V_H$ sequence as shown in SEQ ID NO:1 and a $V_L$ sequence as shown in SEQ ID NO:2.

19. The method of claim 17, wherein the administration of the effective amount of the anti-ErbB3 antibody suppresses growth of the breast cancer tumor.

20. The method of claim 17, which further comprises administering to the patient an effective amount of at least one additional anti-cancer agent.

21. The method of claim 20, wherein the at least one additional anti-cancer agent is a taxane.

22. The method of claim 21, wherein the taxane is paclitaxel.

* * * * *